US010806635B2

(12) United States Patent
Schneider et al.

(10) Patent No.: US 10,806,635 B2
(45) Date of Patent: Oct. 20, 2020

(54) METHODS AND APPARATUSES FOR SEPARATING AND POSITIONING DISCRETE ARTICLES

(71) Applicant: The Procter & Gamble Company, Cincinnati, OH (US)

(72) Inventors: Uwe Schneider, Cincinnati, OH (US); Noble Lester Rye, II, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 352 days.

(21) Appl. No.: 15/456,644

(22) Filed: Mar. 13, 2017

(65) Prior Publication Data

US 2017/0266055 A1    Sep. 21, 2017

Related U.S. Application Data

(60) Provisional application No. 62/308,272, filed on Mar. 15, 2016.

(51) Int. Cl.
*A61F 13/15*       (2006.01)
*B65H 39/14*       (2006.01)
(Continued)

(52) U.S. Cl.
CPC .. *A61F 13/15723* (2013.01); *A61F 13/15764* (2013.01); *B23K 26/0619* (2015.10);
(Continued)

(58) Field of Classification Search
CPC .............. B26D 1/405; A61F 13/15723; A61F 13/15764; B23K 26/0619; B23K 26/0846;
(Continued)

(56) References Cited

U.S. PATENT DOCUMENTS 3,560,291 A      2/1971  Foglia et al.
4,022,456 A  *   5/1977  Hooper ............. A61F 13/15585
                                                    493/357

(Continued)

FOREIGN PATENT DOCUMENTS

CN       204033619 U    12/2014
EP       0 731 029 B1   6/1998
(Continued)

OTHER PUBLICATIONS

International Search Report and Written Opinion, PCT/US2017/022068, dated May 19, 2017.

*Primary Examiner* — Kenneth E Peterson
*Assistant Examiner* — Fernando A Ayala
(74) *Attorney, Agent, or Firm* — Christian M. Best

(57) ABSTRACT

Methods of separating and positioning discrete articles formed from a continuous length of articles are provided. The methods may comprise the steps of receiving a first portion of the continuous length on a first head in a receiving position of an orbit about a first rotational axis and receiving a second portion of the continuous length on a second head in the receiving position of the orbit about the first rotational axis. The methods may comprise providing a laser system configured to produce and direct a laser beam, and ablating a portion of the continuous length of articles intermediate the first head and the second head with the laser beam to separate the first portion of the continuous length of articles from the second portion of the continuous length of articles, thereby forming a discrete article on the first head.

19 Claims, 12 Drawing Sheets

(51) Int. Cl.
  *B65H 29/24* (2006.01)
  *B23K 26/06* (2014.01)
  *B23K 26/364* (2014.01)
  *B23K 26/08* (2014.01)
  *B23K 26/38* (2014.01)
  *B26D 1/40* (2006.01)

(52) U.S. Cl.
  CPC ........ *B23K 26/0846* (2013.01); *B23K 26/364* (2015.10); *B23K 26/38* (2013.01); *B65H 29/241* (2013.01); *B65H 39/14* (2013.01); *B26D 1/405* (2013.01); *B65H 2406/3454* (2013.01)

(58) Field of Classification Search
  CPC ............... B23K 26/364; B23K 26/38; B65H 2406/3454; B65H 29/241; B65H 39/14
  See application file for complete search history.

(56) References Cited

U.S. PATENT DOCUMENTS

| | | | |
|---|---|---|---|
| 5,393,360 A | 2/1995 | Bridges et al. | |
| 5,760,369 A | 6/1998 | Wenkman | |
| 5,767,481 A | 6/1998 | Graf | |
| 5,944,278 A | 8/1999 | Stevens, III et al. | |
| 6,056,682 A * | 5/2000 | Belanger | B26D 1/605 493/340 |
| 6,098,557 A | 8/2000 | Couillard et al. | |
| 6,191,382 B1 | 2/2001 | Damikolas | |
| 6,303,901 B1 | 10/2001 | Perry et al. | |
| 6,388,231 B1 | 5/2002 | Andrews | |
| 6,414,264 B1 | 7/2002 | Von Falkenhausen | |
| 6,517,659 B1 | 2/2003 | VanderWerf et al. | |
| 6,524,443 B2 | 2/2003 | Doelle et al. | |
| 6,648,122 B1 * | 11/2003 | Hirsch | B65G 47/848 156/552 |
| 6,820,671 B2 * | 11/2004 | Calvert | A61F 13/15772 156/543 |
| 6,979,798 B2 | 12/2005 | Gu et al. | |
| 7,032,278 B2 | 4/2006 | Kurtz, Jr. | |
| 7,049,543 B2 | 5/2006 | Roos et al. | |
| 7,144,479 B2 | 12/2006 | Davis et al. | |
| 7,216,685 B2 * | 5/2007 | Nakakado | A61F 13/15593 156/494 |
| 7,306,388 B2 | 12/2007 | Acher | |
| 7,310,858 B2 | 12/2007 | Fleissner | |
| 7,563,695 B2 | 7/2009 | Gu et al. | |
| 7,615,128 B2 | 11/2009 | Mikkelsen | |
| 7,971,333 B2 | 7/2011 | Gale et al. | |
| 8,026,459 B2 | 9/2011 | Tanaka et al. | |
| 8,168,961 B2 | 5/2012 | Straw et al. | |
| 8,329,600 B2 | 12/2012 | Gu et al. | |
| 8,445,812 B2 | 5/2013 | Lupinetti et al. | |
| 8,536,024 B2 | 9/2013 | Nagatomo et al. | |
| 8,540,612 B2 | 9/2013 | Skopek et al. | |
| 8,629,416 B2 | 1/2014 | Straw et al. | |
| 8,739,574 B2 | 6/2014 | Liu et al. | |
| 8,757,307 B2 | 6/2014 | Winter et al. | |
| 8,822,009 B2 | 9/2014 | Riviere et al. | |
| 9,149,394 B2 | 10/2015 | Rosani et al. | |
| 9,198,782 B2 | 12/2015 | Kline et al. | |
| 9,999,551 B2 | 6/2018 | Papsdorf et al. | |
| 2003/0047695 A1 | 3/2003 | Zik et al. | |
| 2003/0079330 A1 * | 5/2003 | Stopher | B65H 39/14 29/430 |
| 2004/0026384 A1 | 2/2004 | Mueller et al. | |
| 2004/0118820 A1 | 6/2004 | Wojcik et al. | |
| 2004/0159637 A1 | 8/2004 | Herke et al. | |
| 2004/0159998 A1 | 8/2004 | Khalid | |
| 2004/0245069 A1 * | 12/2004 | Hook | A61F 13/15764 198/459.1 |
| 2005/0082141 A1 * | 4/2005 | Dombek | A24C 5/326 198/474.1 |
| 2005/0092146 A1 | 5/2005 | Carbone, II et al. | |
| 2005/0098008 A1 | 5/2005 | Henriksen | |
| 2005/0214511 A1 | 9/2005 | Vogt et al. | |
| 2006/0090868 A1 | 5/2006 | Brownfield et al. | |
| 2006/0283846 A1 | 12/2006 | Lupinetti et al. | |
| 2008/0196564 A1 * | 8/2008 | McCabe | A61F 13/15723 83/23 |
| 2008/0295984 A1 | 12/2008 | Miikki et al. | |
| 2008/0305298 A1 | 12/2008 | Lakashmi et al. | |
| 2009/0050661 A1 * | 2/2009 | Na | B26F 3/002 225/2 |
| 2009/0200280 A1 | 8/2009 | Piantoni et al. | |
| 2009/0283504 A1 | 11/2009 | Matsuo et al. | |
| 2011/0048996 A1 | 3/2011 | Klaus et al. | |
| 2011/0070390 A1 | 3/2011 | Costin, Sr. et al. | |
| 2012/0067699 A1 | 3/2012 | Pasqualoni et al. | |
| 2012/0312869 A1 | 12/2012 | Fike et al. | |
| 2013/0152360 A1 * | 6/2013 | Schoultz | B65H 39/14 29/428 |
| 2013/0277341 A1 | 10/2013 | Dvorkin | |
| 2013/0334739 A1 | 12/2013 | Miller et al. | |
| 2014/0110037 A1 | 4/2014 | Verboomen et al. | |
| 2015/0064387 A1 | 3/2015 | Imai et al. | |
| 2015/0079359 A1 | 3/2015 | Costin, Jr. | |
| 2015/0123318 A1 | 5/2015 | Sestini et al. | |
| 2015/0225890 A1 | 8/2015 | Canonico et al. | |
| 2016/0030252 A1 * | 2/2016 | Sayaovong | A61F 13/15804 83/78 |
| 2016/0068364 A1 | 3/2016 | Schmitz | |
| 2016/0083898 A1 | 3/2016 | Godmaire et al. | |
| 2016/0120709 A1 | 5/2016 | Hamamoto et al. | |
| 2016/0200088 A1 | 7/2016 | Schaede | |
| 2016/0250082 A1 | 9/2016 | Hamamoto et al. | |
| 2016/0278997 A1 | 9/2016 | Wright et al. | |
| 2016/0354258 A1 * | 12/2016 | Findley | B65H 35/08 |
| 2017/0189242 A1 * | 7/2017 | Piantoni | A61F 13/15723 |
| 2017/0304124 A1 * | 10/2017 | Lenser | A61F 13/15764 |

FOREIGN PATENT DOCUMENTS

| | | |
|---|---|---|
| EP | 0 868 251 B1 | 11/2004 |
| EP | 1 820 634 A1 | 8/2007 |
| JP | 2015-008946 A | 1/2015 |
| JP | 2015-008947 A | 1/2015 |
| JP | 2015-009505 A | 1/2015 |
| JP | 56 95163 B1 | 4/2015 |
| JP | 2015-085087 A | 5/2015 |
| JP | 2015-085088 A | 5/2015 |
| JP | 2015-085089 A | 5/2015 |
| JP | 2015-085091 A | 5/2015 |
| JP | 2015-085651 A | 5/2015 |
| JP | 2015-085652 A | 5/2015 |
| JP | 2015-085653 A | 5/2015 |
| JP | 2015-085654 A | 5/2015 |
| JP | 2015-097579 A | 5/2015 |
| JP | 2015-112399 A | 6/2015 |
| JP | 2015-112400 A | 6/2015 |
| JP | 2015-112401 A | 6/2015 |
| WO | WO 2006/083127 A1 | 8/2006 |
| WO | WO 2007/122284 A1 | 11/2007 |
| WO | WO 2011/083205 A1 | 7/2011 |
| WO | WO 2012/049267 A1 | 4/2012 |
| WO | WO 2012/070462 A1 | 5/2012 |
| WO | WO 2014/001217 A1 | 1/2014 |
| WO | WO 2014/103818 A1 | 7/2014 |
| WO | WO 2014/208635 A1 | 12/2014 |
| WO | WO 2014/208636 A1 | 12/2014 |
| WO | WO 2014/208637 A1 | 12/2014 |
| WO | WO 2014/208639 A1 | 12/2014 |
| WO | WO 2014/208640 A1 | 12/2014 |
| WO | WO 2014/208641 A1 | 12/2014 |
| WO | WO 2014/208642 A1 | 12/2014 |
| WO | WO 2014/208650 A1 | 12/2014 |
| WO | WO 2014/208651 A1 | 12/2014 |
| WO | WO 2014/208652 A1 | 12/2014 |

* cited by examiner

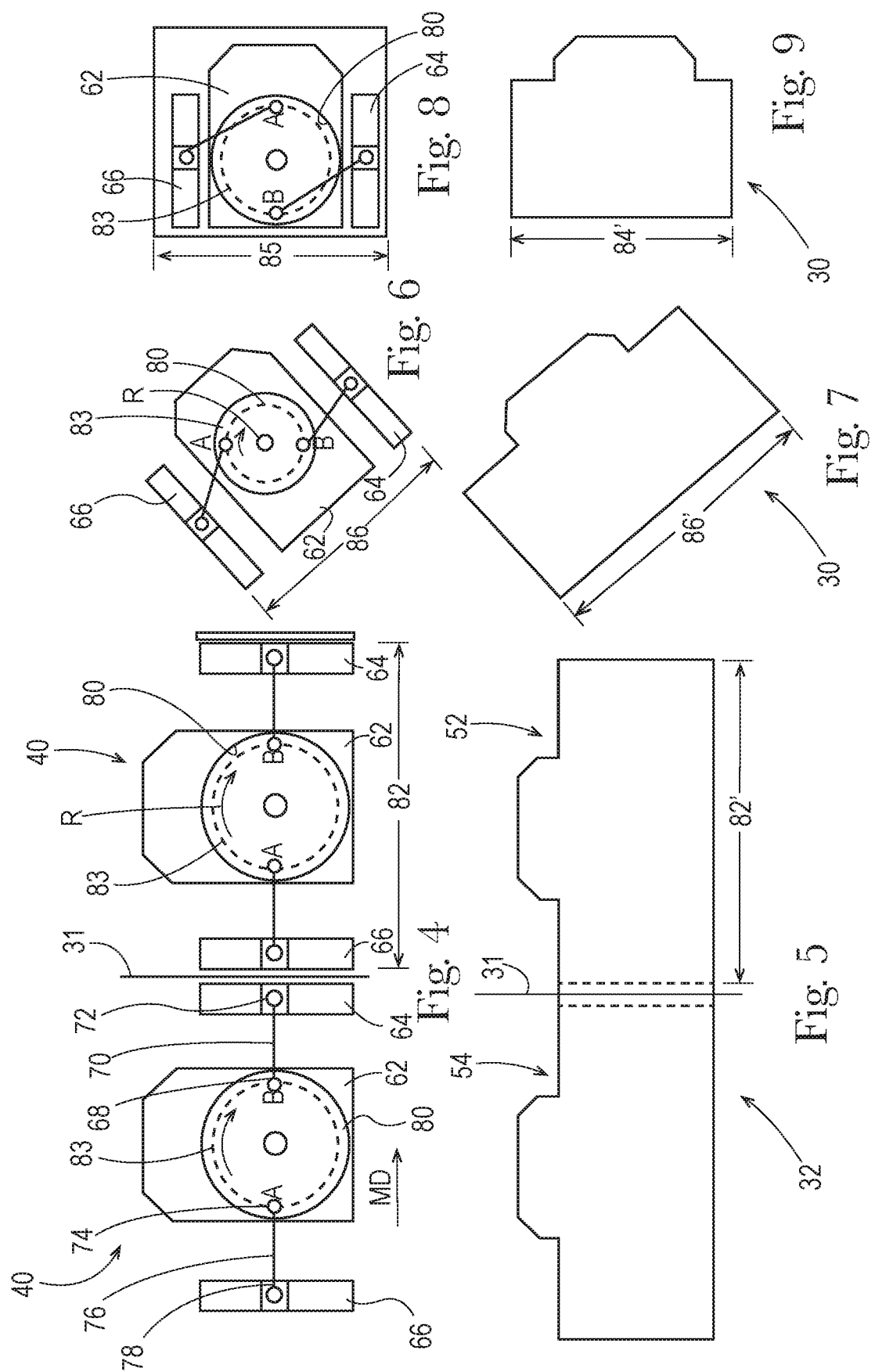

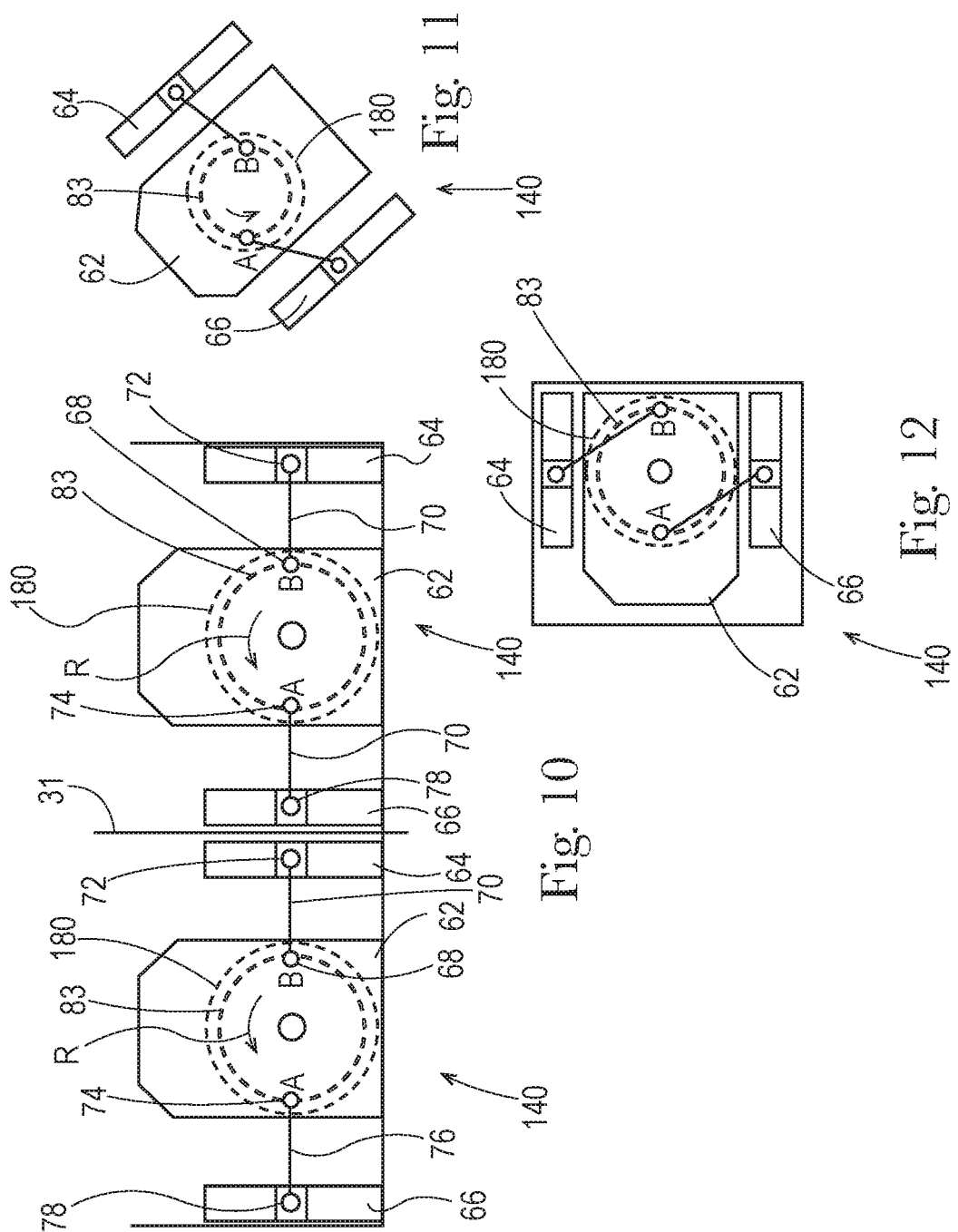

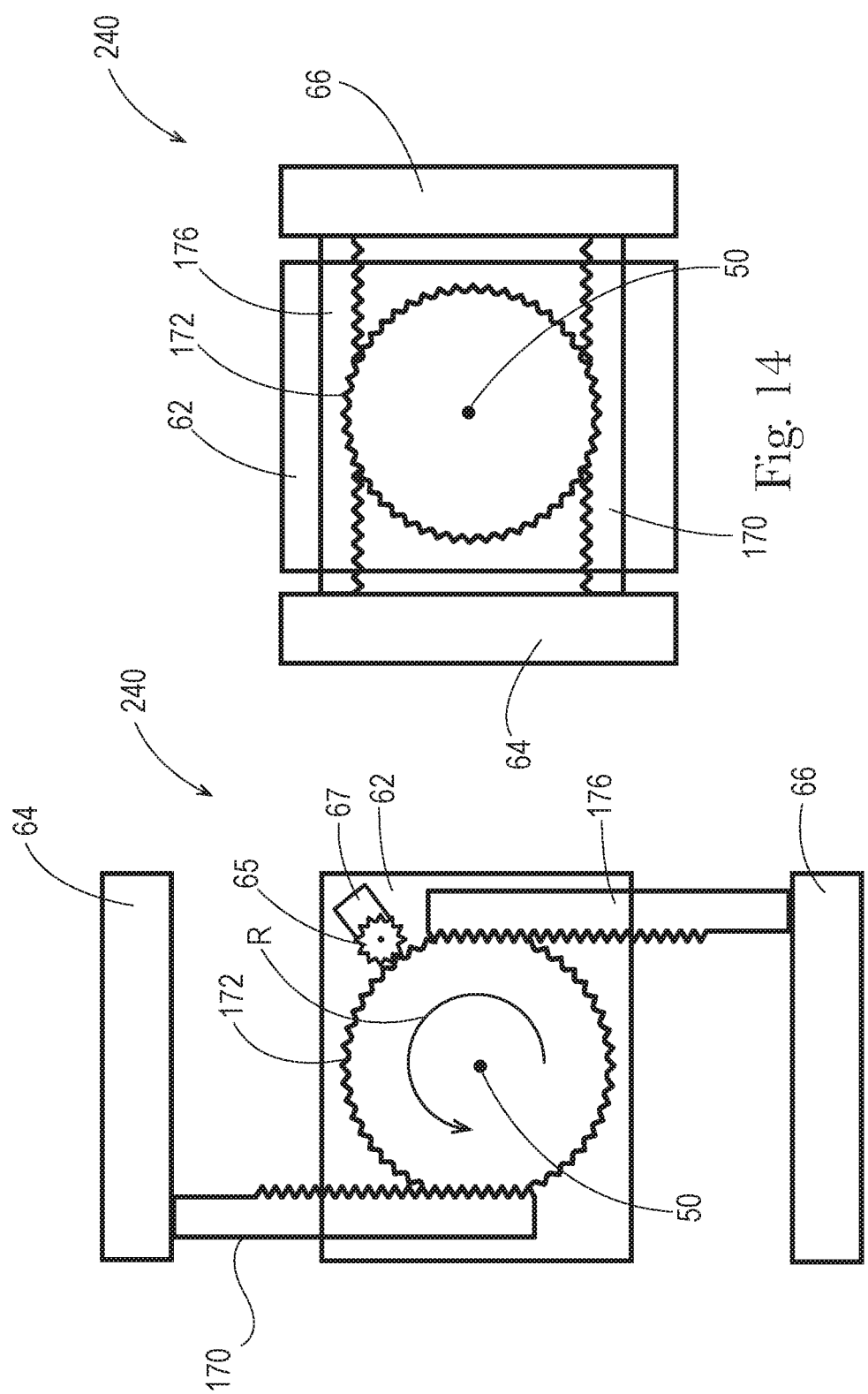

METHODS AND APPARATUSES FOR SEPARATING AND POSITIONING DISCRETE ARTICLES

CROSS REFERENCE TO RELATED APPLICATION

This application claims the benefit, under 35 U.S.C. § 119(e), to U.S. Provisional Patent Application No. 62/308,272, filed on Mar. 15, 2016, which is herein incorporated by reference in its entirety.

FIELD

The present disclosure generally relates to methods and apparatuses for separating and positioning discrete articles and, more particularly, relates to methods and apparatuses for separating and positioning discrete articles formed from a continuous length of articles.

BACKGROUND

Referring to FIG. 1, discrete articles 10, such as diapers or components thereof, are sometimes formed from a continuous length of the articles 12 (e.g., a web of diapers) or components of the articles (e.g., a web of ear components for diapers) (together hereinafter referred to as a continuous length of articles). Sometimes, the continuous length of the articles 12 is advanced in a machine direction (MD) to a transfer assembly 14 with rotating heads 16 and is then cut, using mechanical processes, to cut the continuous length of the articles 12 into a plurality of discrete articles 10. Each discrete article 10 may be positioned on one of the heads 16 of the transfer assembly 14 after being cut from the continuous length of the articles 12. In some instances, the discrete articles 10 may also need to be rotated into a suitable orientation for further processing. The transfer assembly 14 may be used to pick up a portion of the continuous length of the articles 12, cut it to form a discrete article 10, and then rotate the discrete article 10 into a suitable orientation. The transfer assembly 14 uses mechanical processes to effectuate the cutting. Typically, a knife roll 18 and a plurality of anvil bars 20 are used. The anvil bars 20 may be positioned on the transfer assembly 14 intermediate the heads 16 and may rotate with the heads 16. One issue with the use of the knife roll 18 and anvil bars 20 is that the transfer assembly 14 must be able to withstand very high forces generated by severing a portion of the continuous length of articles 12 between a blade 22 of the knife roll 18 and an anvil bar 20. The transfer assembly 14 must have a heavy duty construction to withstand these high forces. This causes the transfer assembly 14 to be more expensive to manufacture and more difficult to rotate because of its weight, including the weight of the bulky anvil bars 20. Furthermore, mechanical cutting processes require precision within a few microns to achieve acceptably pitched discrete articles 10, owing to the fact that the blade 22 has to contact the anvil bar 20 at the exact proper location. Additionally, heads 16 of the transfer assembly 14 that receive a portion of the continuous length of the articles 12 are typically not adjustable. Thus, in some instances, when a discrete article 10 is cut from the continuous length of the articles 12, control of the discrete article 10 is less than desired. Furthermore, the transfer assembly 14 has very limited pitch ranges of products it can process in view of the non-adjustability of the heads. As a result, the transfer assembly 14 has to be changed out to process a differently sized discrete article, which can lead to an excessive amount of downtime. What is needed are methods and apparatuses for separating and positioning discrete articles from a continuous length of articles that overcome the above-mentioned disadvantages.

SUMMARY

The present disclosure provides methods and apparatuses for separating and positioning discrete articles from a continuous length of articles that overcome the above-mentioned disadvantages. The present disclosure provides anvil-less methods of separating a portion of a continuous length of articles into discrete articles, thereby eliminating the requirement for a knife roll and a plurality of anvil bars on a transfer assembly. By "anvil-less", it is meant that no anvil bars or other anvil-like surfaces are required for separation. Stated another way, the separation process does not require a member behind what is being separated. Some examples of anvil-less methods of separation comprise the use of laser systems, hot air separation systems, hot wire separation systems, high pressure water jet separation systems, traversing slitters, and/or log saws. Further details regarding log saw are described in U.S. Pat. No. 3,213,734 to Nystrand, U.S. Pat. No. 5,458,033 to Wierschke, and U.S. Pat. No. 6,123,002 to Wunderlich et al, for example. The use of these anvil-less methods of separation eliminate the need for transfer assemblies to be constructed to withstand high forces caused by the knife roll and anvil bars and thus, may be made more cost-effective and may be easier to operate owing to their reduced weight. Additionally, the use of anvil-less methods of separation reduces the precision required during separation compared to related art knife rolls and anvil bars used for cutting, while still achieving a suitable discrete article pitch. This is because the anvil-less methods separate the continuous length of articles between adjacent heads without the need for matching the rotating of an anvil bar. The heads of the transfer assemblies (e.g., transfer units, turning units, or turning and repitching units) of the present disclosure are also able to maintain better control over the discrete articles once separated from the continuous length of articles. These heads are capable of movement between at least a first configuration and a second configuration. The first configuration may be more expanded than the second configuration. Thus, in the first configuration, the discrete article may be stretched to or maintained at a first pitch length, and in the second configuration, the discrete articles may be stretched to or maintained at a second pitch length. The first pitch length may be greater than the second pitch length, but the second pitch length may still maintain enough stretch to maintain adequate control over the discrete articles. Furthermore, by using the anvil-less method of separating to separate the continuous length of articles, in combination with the adjustable heads, the transfer assemblies of the present disclosure can process a large range (e.g., +/−100 mm to +/−700 mm, for example) of discrete article sizes and/or pitch lengths without the need for change outs, in some cases allowing for customization of discrete articles using a single transfer assembly. This can significantly reduce downtime on a discrete article processing line. The customization, for example, may be producing discrete articles having two or more different sizes or configuration using the same transfer assembly. Further details regarding customizable discrete articles, or portions thereof, that may be produced using the methods of the present disclosure may be found in European Patent Application No. 15169520.2, to Schmidt et al., filed on May 28, 2015.

As an example of one anvil-less method of separation, the present disclosure provides a laser system comprising a laser source and a one or more scan heads. The laser source is configured to emit a laser beam to the scan head and the scan head is configured to direct the laser beam. The laser beam may be directed by the scan head such that it ablates a portion of a continuous length of articles into discrete articles, thereby eliminating the requirement for a knife roll and a plurality of anvil bars on a transfer assembly.

In a form, the present disclosure is directed, in part, to a method of separating and positioning discrete articles formed from a continuous length of articles. The method may comprise the steps of advancing the continuous length of articles in a machine direction, providing a transfer assembly comprising a frame defining a first rotational axis, a first head comprising a first transfer surface, and a second head comprising a second transfer surface. The first transfer surface may define a first plurality of fluid ports and the second transfer surface may define a second plurality of fluid ports. The method may comprise the steps of orbiting the first head about the first rotational axis, orbiting the second head about the first rotational axis, applying a fluid pressure to the first plurality of fluid ports, and applying a fluid pressure to the second plurality of fluid ports. The method may comprise the steps of receiving a first portion of the continuous length of articles on the first transfer surface of the first head in a receiving position of the orbit about the first rotational axis and subsequently, receiving a second portion of the continuous length of articles on the second transfer surface of the second head in the receiving position of the orbit about the first rotational axis. The method may comprise providing a laser system configured to produce and direct a laser beam, and ablating a portion of the continuous length of articles intermediate the first head and the second head with the laser beam to separate the first portion of the continuous length of articles from the second portion of the continuous length of articles, forming a discrete article on the first head. The ablating step may comprise traversing the portion of the continuous length of articles with the laser beam from a first side of the continuous length of articles to a second, opposite side of the continuous length of articles. The method may comprise the step of rotating the first head and the discrete article about a second rotational axis during the orbiting about the first rotational axis. The first rotational axis may extend in a first direction, and the second rotational axis may extend in a second, different direction. The method may comprise the step of placing the discrete article on a moving carrier member in a depositing position of the orbit about the first rotational axis.

In a form, the present disclosure is directed, in part, to a method of separating and positioning discrete articles formed from a continuous length of articles. The method may comprise the steps of advancing the continuous length of articles in a machine direction and providing a transfer assembly. The transfer assembly may comprise a frame defining a first rotational axis, a first head comprising a first transfer surface, and a second head comprising a second transfer surface. The method may comprise orbiting the first head about the first rotational axis and orbiting the second head about the first rotational axis. The method may comprise receiving a first portion of the continuous length of articles on the first transfer surface of the first head in a receiving position of the orbit about the first rotational axis and subsequently, receiving a second portion of the continuous length of articles on the second transfer surface of the second head in the receiving position of the orbit about the first rotational axis. The method may comprise providing a laser system configured to produce and direct a laser beam, and ablating a portion of the continuous length of articles intermediate the first head and the second head with the laser beam to separate the first portion of the continuous length of articles from the second portion of the continuous length of articles, forming a discrete article on the first head. The ablating step may comprise traversing the portion of the continuous length of articles with the laser beam at an angle relative to a cross-machine direction and the machine direction from a first side of the continuous length of articles to a second, opposite side of the continuous length of articles. The method may comprise placing the discrete article on a moving carrier member in a depositing position of the orbit about the first rotational axis.

In a form, the present disclosure is directed, in part, to a method of separating and positioning discrete articles formed from a continuous length of articles. The method may comprise the steps of advancing the continuous length of articles in a machine direction and providing a transfer assembly. The transfer assembly may comprise a frame defining a first rotational axis, a first head comprising a first transfer surface, and a second head comprising a second transfer surface. The first transfer surface may define a first plurality of fluid ports. The second transfer surface may define a second plurality of fluid ports. The method may comprise orbiting the first head about the first rotational axis, orbiting the second head about the first rotational axis, applying a fluid pressure to the first plurality of fluid ports, and applying a fluid pressure to the second plurality of fluid ports. The method may comprise receiving a first portion of the continuous length of articles on the first transfer surface of the first head in a receiving position of the orbit about the first rotational axis and subsequently, receiving a second portion of the continuous length of articles on the second transfer surface of the second head in the receiving position of the orbit about the first rotational axis. The method may comprise using a means for separating a portion of the continuous length of articles intermediate the first head and the second head to separate the first portion of the continuous length of articles from the second portion of the continuous length of articles, forming a discrete article on the first head. The means for separating may traverse the portion of the continuous length of articles from a first side of the continuous length of articles to a second, opposite side of the continuous length of articles. The method may comprise rotating the first head and the discrete article about a second rotational axis during the orbiting about the first rotational axis. The first rotational axis may extend in a first direction and the second rotational axis may extend in a second, different direction. The method may comprise placing the discrete article on a moving carrier member in a depositing position of the orbit about the first rotational axis.

In a form, the present disclosure is directed, in part, to a method of separating and positioning discrete articles formed from a continuous length of articles. The method may comprise the steps of advancing the continuous length of articles in a machine direction, providing a transfer assembly comprising a frame defining a first rotational axis, a first head comprising a first transfer surface, and a second head comprising a second transfer surface. The first transfer surface may define a first plurality of fluid ports and the second transfer surface may define a second plurality of fluid ports. The method may comprise the steps of orbiting the first head about the first rotational axis, orbiting the second head about the first rotational axis, applying a fluid pressure to the first plurality of fluid ports, and applying a fluid pressure to the second plurality of fluid ports. The method may comprise the steps of receiving a first portion of the continuous length of articles on the first transfer surface of the first head in a receiving position of the orbit about the first rotational axis and subsequently, receiving a second portion of the continuous length of articles on the second transfer surface of the second head in the receiving position of the orbit about the first rotational axis. The method may comprise providing an anvil-less separation means, and separating a portion of the continuous length of articles intermediate the first head and the second head with the anvil-less separation means to separate the first portion of the continuous length of articles from the second portion of the continuous length of articles, forming a discrete article on the first head. The method may comprise the step of rotating the first head and the discrete article about a second rotational axis during the orbiting about the first rotational axis. The first rotational axis may extend in a first direction, and the second rotational axis may extend in a second, different direction. The method may comprise the step of placing the discrete article on a moving carrier member in a depositing position of the orbit about the first rotational axis.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 4 is a top view schematic illustration of a first head and a second head, both in a first, expanded configuration in accordance with the present disclosure;

FIG. 5 is a top view schematic illustration of first and second portions of the continuous length of articles positioned on the first head and the second heads, respectively, in accordance with the present disclosure;

FIG. 6 is a top view schematic illustration of the first head of FIG. 4 in a partially rotated position in accordance with the present disclosure;

FIG. 7 is a top view schematic illustration of a discrete article after it is separated from the continuous length of articles and positioned on the first head of FIG. 6 in accordance with the present disclosure;

FIG. 8 is a top view schematic illustration of the first head of FIG. 6 in a fully rotated position and a second, contracted configuration in accordance with the present disclosure;

FIG. 9 is a top view schematic illustration of the discrete article of FIG. 7 and positioned on the first head of FIG. 8 in accordance with the present disclosure;

FIG. 10 is a top view schematic illustration of another first head and another second head, both in a first, expanded configuration in accordance with the present disclosure;

FIG. 11 is a top view schematic illustration of the first head of FIG. 10 in a partially rotated position in accordance with the present disclosure;

FIG. 12 is a top view schematic illustration of the first head of FIG. 11 in a fully rotated position and a second, contracted configuration in accordance with the present disclosure;

FIG. 13 is a top view schematic illustration of yet another first head and yet another second head, both in a first, expanded configuration in accordance with the present disclosure;

FIG. 14 is a top view schematic illustration of the first head of FIG. 13 in a fully rotated position and a second, contracted configuration in accordance with the present disclosure;

DETAILED DESCRIPTION

Figure 1:
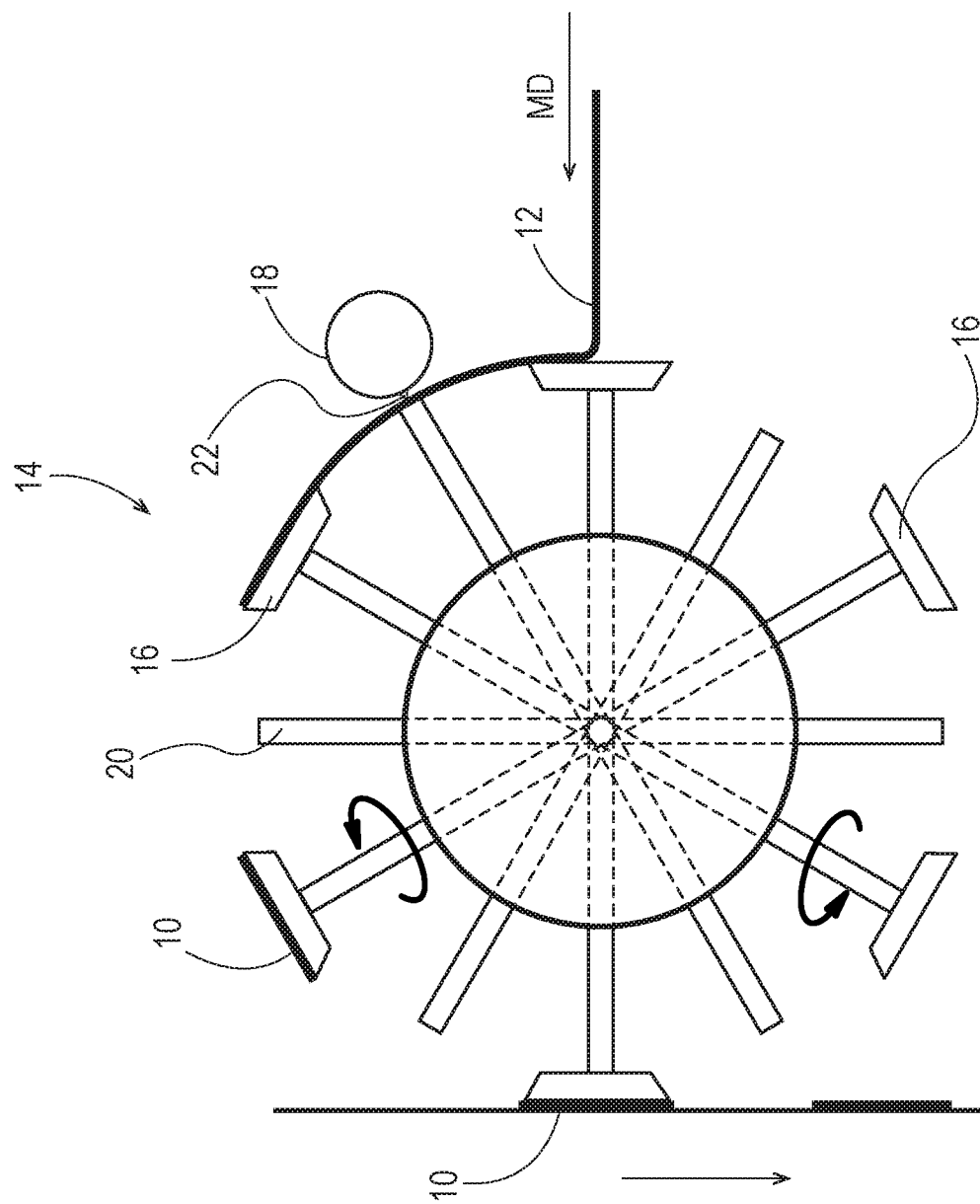
FIG. 1 is a front view schematic illustration of a prior art transfer assembly having a plurality of heads, a knife roll, and anvil bars, wherein the transfer assembly is configured to cut and position discrete articles formed from a continuous length of articles.

Various non-limiting forms of the present disclosure will now be described to provide an overall understanding of the principles of the structure, function, manufacture, and use of the methods and apparatuses for separating and positioning discrete articles disclosed herein. One or more examples of these non-limiting forms are illustrated in the accompanying drawings. Those of ordinary skill in the art will understand that methods and apparatuses for separating and positioning discrete articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

The term "absorbent article(s)" is used herein to refer to consumer products whose primary function is to absorb and retain bodily exudates and wastes. Absorbent articles as used herein may refer to pants, taped diapers, and/or sanitary napkins (e.g., feminine hygiene products). The terms "diaper" and "pants" are used herein to refer to absorbent articles generally worn by infants, children, and incontinent persons about the lower torso.

The term "machine direction" (MD) is used herein to refer to the primary direction of material, web, or article flow through a process. In various manufacturing and converting processes, such as a bi-fold process, it may be possible to have more than one machine direction when an article is undergoing simultaneous processes. In other words, a manufacturing line may have an overall machine direction, but a material or an article may travel in directions other than the overall machine direction as it passes through various processes along the manufacturing line. For example, a discrete article having a trailing end portion and a leading end portion, each portion being attached to the surface of a different roll and/or conveyor may travel in two different directions simultaneously. In this example, both directions of travel may be considered the machine direction.

The term "cross direction" (CD) is used herein to refer to a direction that is generally perpendicular to the machine direction.

The term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers disclosed in various suitable configurations are disclosed in U.S. Pat. Nos. 5,167,897, 5,360, 420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" refers herein to disposable absorbent articles having a continuous perimeter waist opening and continuous perimeter leg openings designed for infant, child, or adult wearers. A pant may be configured with a continuous or closed waist opening and at least one continuous, closed, leg opening prior to the article being applied to the wearer. A pant may be preformed by various techniques including, but not limited to, joining together portions of the absorbent article using any refastenable and/or permanent closure member (e.g., seams, heat bonds, pressure welds, adhesives, cohesive bonds, mechanical fasteners, etc.). A pant may be preformed anywhere along the circumference of the absorbent article in the waist region (e.g., side fastened or seamed, front waist fastened or seamed, rear waist fastened or seamed). A pant may be opened about one or both of the side seams and then refastened. Example pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

The term "discrete articles" refers herein to absorbent articles, pants, taped diapers, sanitary napkins, bandages, medical pads and dressings, and any other suitable articles, in any industry, capable of being transferred using the transfer apparatuses of the present disclosure. Discrete articles may also refer herein to portions of the absorbent articles, pants, taped diapers, sanitary napkins, bandages, medical pads and dressings, and other suitable articles. The discrete articles may be flexible. In one example, discrete articles may refer herein to a chassis of a taped diaper or a pant. The chassis may comprise a topsheet, a backsheet, and an absorbent core disposed between at least a portion of the topsheet and the backsheet. The chassis may also comprise stretched elastic elements such as leg elastics and inner barrier leg cuff elastics, for example.

Methods and apparatuses for anvil-less separating and positioning discrete articles formed from a continuous length of articles are provided by the present disclosure. The discrete articles may be any suitable articles, such as taped diapers, pants, cleaning pads, dusting pads, sanitary napkins, any other suitable products, or consumer products, that are suitable for the methods described herein, and/or components of any of the same. These methods and apparatuses of the present disclosure may decrease the precision required during anvil-less separating of the discrete articles from a continuous length of articles in view of the laser ablating techniques described herein. By separating the continuous length of the articles using anvil-less methods of separation, such as laser beams, the anvil bars 20 and knife roll 22 of FIG. 1 are no longer required. Thus, the transfer assemblies of the present disclosure do not have to withstand the very high forces of the knife roll 22 contacting the anvil bars 22, are easier to rotate, and can have a less rigid and lighter construction. Furthermore, the methods and apparatuses provide significantly increased pitch capabilities owing to the provision of adjustable heads. This can significantly reduce downtime caused by frequent change-outs of related art transfer devices when changing from 1 size of discrete articles to another.

Figure 2:
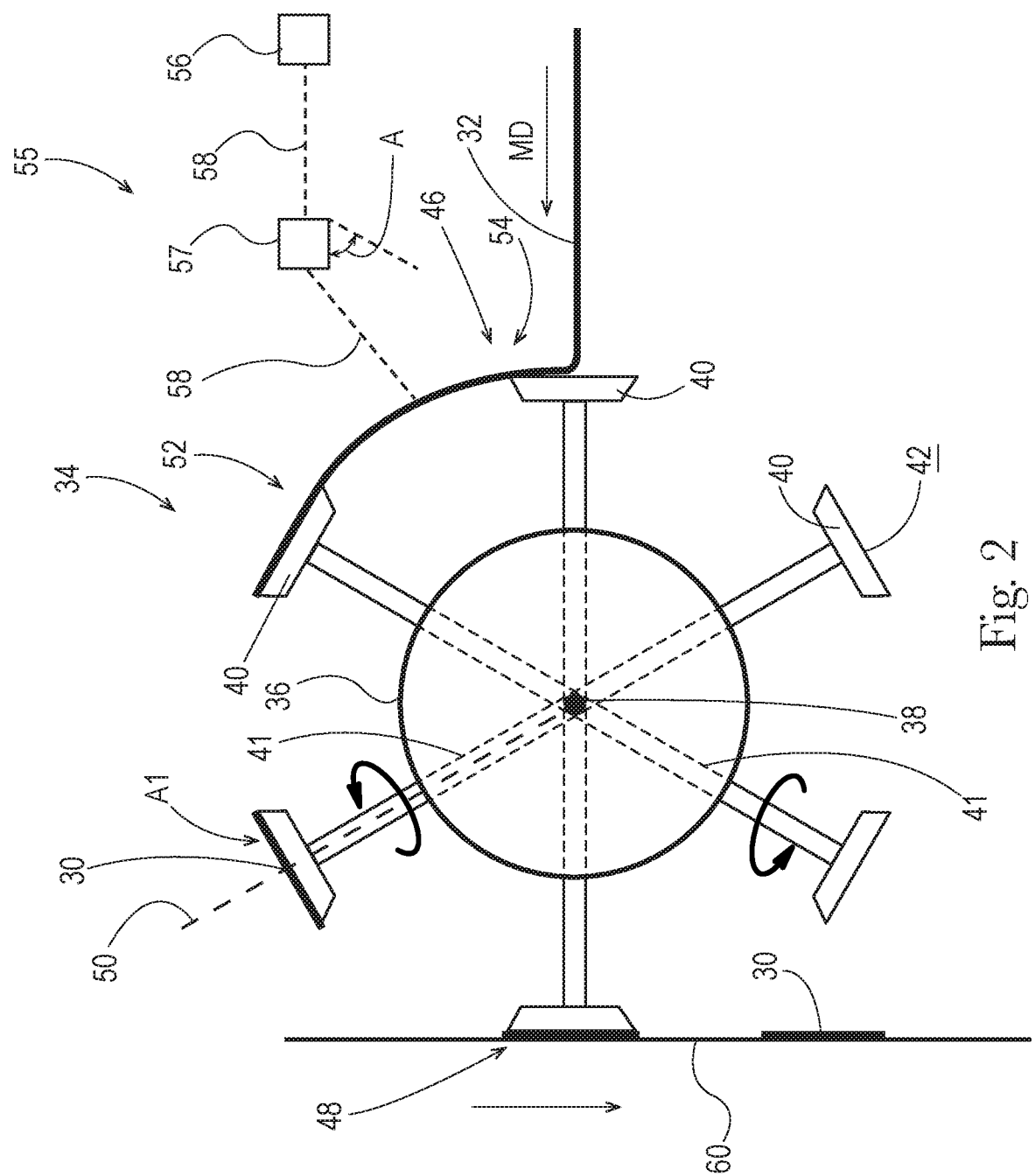
FIG. 2 is a front view schematic illustration of a transfer assembly having a plurality of heads and a laser system in accordance with the present disclosure, wherein the transfer assembly is configured to separate and position discrete articles formed from a continuous length of articles.
Figure 3:
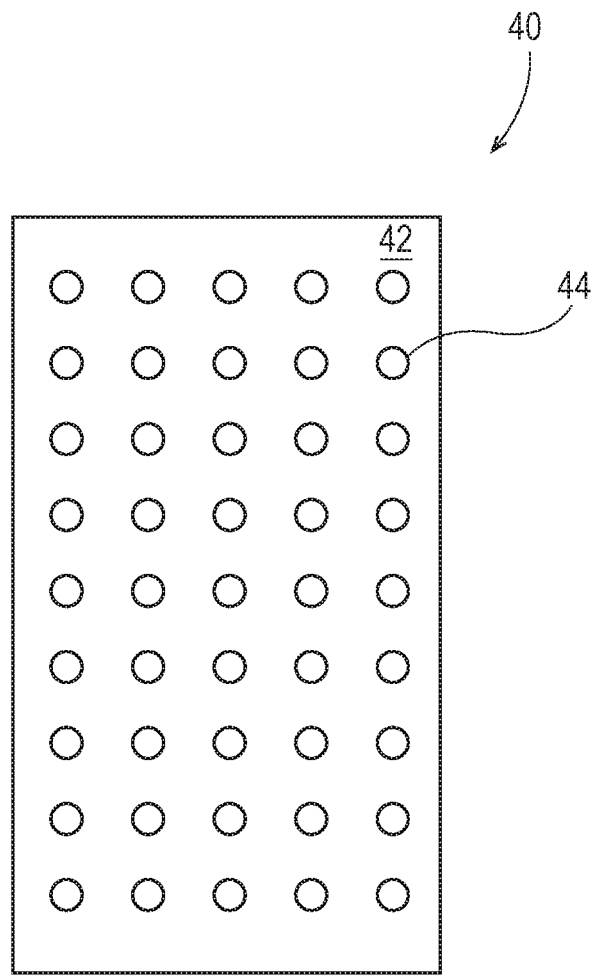
FIG. 3 is a top view of a transfer surface of one of the heads of the transfer assembly of FIG. 2 in accordance with the present disclosure.

Referring to FIG. 2, an example method and apparatus for separating and positioning discrete articles 30 formed from a continuous length of articles 32 is provided. First, the continuous length of articles 32 may be advanced or conveyed in a machine direction (MD) toward a transfer assembly 34. The transfer assembly 34 may comprise a frame 36 defining a first rotational axis 38 and a plurality of heads 40. Each of the heads 40 may comprise a transfer surface 42 configured to receive a portion of the continuous length of articles 32 and thereby discrete articles 30, once cut from the continuous length of articles 32. The transfer surface 42 may be flat, arcuate, or have both flat and arcuate portions. The transfer surface 42 may have more curvature in the MD or CD in any position of the heads 40. Referring to FIG. 3, a plurality of fluids ports 44 may be defined in each of the transfer surfaces 42, or in at least some of the transfer surfaces 42. The fluid ports 44 may be in fluid communication with a fluid movement device, such as a vacuum pump, for example. The fluid movement device may provide a fluid pressure to a vacuum manifold on the transfer assembly 34, which may then provide the fluid pressure to the heads 40 and to the plurality of the fluid ports 44. The fluid ports 44 may provide a positive fluid pressure, a negative fluid pressure, and/or may provide zones of positive fluid pressure and zones of negative fluid pressure. In some instances, the same zone of fluid ports 44 may be configured to provide a negative fluid pressure at a certain time and a positive fluid pressure at another certain time. The positive fluid pressure may be helpful when transferring discrete articles off of the heads 40, while the negative fluid pressure may be helpful in obtaining the continuous length of the articles 32 and holding and controlling the discrete articles 30, once separated from the continuous length of the articles 32. In some instances, the fluid pressure may be provided to certain fluid ports on the rotating heads depending on the size of the discrete article being transferred. For example, when smaller sized discrete articles are being transferred, outer fluid ports on the rotating heads may not receive a fluid pressure, and when larger sized discrete articles are being transferred, these same outer fluid ports may receive the fluid pressure. Further details regarding such heads and fluid systems can be found in U.S. patent application Ser. No. 62/261,444, to Schneider et al., filed on Dec. 1, 2015. Alternatively, fluid ports may not be provided and adhesives may be used on the discrete articles and/or the transfer surfaces 42 to maintain control of the discrete articles. In still other instances, static charges on the transfer surfaces 42 or the discrete articles may be used to maintain control of the discrete articles. In yet other instances, mechanical clamps may be used to retain the discrete articles 30 (or lengths thereof) to the heads 40 and/or to maintain control of the discrete articles.

Referring again to FIG. 2, the plurality of heads 40 may be orbited about the first rotational axis 38. The heads 40 may travel through a receiving position 46 and a depositing position 48 during their orbit about the first rotational axis 38. The heads 40 may be orbited about the first rotational axis 38, or at least partially about the first rotational axis 38, at a constant angular velocity or at a variable angular velocity. In certain circumstances, the heads 40 may be orbited at a constant angular velocity during a first portion of the orbit and may be orbited at a variable angular velocity during a second portion of the orbit. In some instances, it may be desired to radially displace the heads 40 between the receiving position 46 and the depositing position 48 such that the heads 40 can clear each other during rotation of the heads 40 about a second rotational axis 50. Stated another way, the heads 40 may be moved radially outwardly and/or radially inwardly relative to the first rotational axis 38 such that the heads 40 can clear each other during rotation about the second rotational axis 50. As an example, this radial movement may be accomplished by using a spline mechanism in arms 41 attached to the heads 40. The spline mechanisms may be operatively engaged with a cam, for example, to provide the heads 40 with radial movement relative to the first rotational axis 38, as the heads 40 orbit about the first rotational axis 38. In some instances with or without radial displacement of the heads 40, the angular velocity of certain heads may be increased or decreased during rotation of the heads 40 about the second rotational axis 50 to provide clearance for head rotation. The heads 40, in some instances, may be rotated 90 degrees, about 90 degrees, or another angle, about the second rotational axis 50 between the receiving position 46 and the depositing position 48 and then may be rotated 90 degrees, about 90 degrees, or another angle, about the second rotational axis 50, in the opposite direction (or the same direction) between the depositing position 48 and the receiving position 46. This may be accomplished using, for example, a gearbox operably engaged with the arms 41. The first rotational axis 38 may extend in a first direction and the second rotational axis 50 may extend in a second, different direction. The first direction may be perpendicular to, or substantially perpendicular to, the second direction, for example. In some instances, the heads 40 may not rotate at all between the receiving position 46 and the depositing position 48 or between the depositing position 48 and the receiving position 46.

In addition to rotating the heads 40 between the receiving position 46 and the depositing position 48 about the second rotational axis 50, the discrete articles 30 may also be repitched depending on the process requirements downstream of the transfer assembly 34. An example unit that rotates and repitches discrete articles is fully described in U.S. Pat. No. 8,820,513 to Papsdorf et al.

In operation, still referring to FIG. 2, a first portion 52 of the continuous length of articles 32 may be received on a first transfer surface 42 of a first head 40 in the receiving position 46 of the orbit about the first rotational axis 38 and, subsequently, a second portion 54 of the continuous length of articles 32 may be received on a second transfer surface 42 of a second head 40 in the receiving position 46 of the orbit about the first rotational axis 38. A laser system 55 comprising a laser source 56 and one or more scan heads 57 may be provided. The laser source 56 may be configured to emit a laser beam 58 to the scan head 57 and the scan head 57 may be configured to direct the laser beam 58 to a suitable location (or locations) or in a suitable path across the continuous length of articles 32. The laser system 55 or at least the scan head 57 may be positioned proximate to the receiving position 46, such that the laser beam 58 may be directed towards a portion of the continuous length of articles 32 intermediate the first head 40 and the second head 40, or to other suitable portions of the continuous length of articles 32. In other instances, multiple laser systems may be provided on portions of the transfer assembly, such as between each of the heads. In such an instance, at least the scan heads of the laser system would orbit about the first rotational axis 38.

In an event, the laser beam 58 emitted by the laser system 55 is configured to ablate and/or melt a portion of the continuous length of articles 32 between the first portion 52 and the second portion 54 to separate a discrete article 30 from the continuous length of articles 32. The ablating and/or melting may occur intermediate the first head 40 and the second head 40. No anvils are required to be positioned on an opposite side of the continuous length of articles 32 as the laser beam 58 for adequate ablating and/or melting, unlike the conventional mechanical separation described above with respect to FIG. 1. In some instances, an optional backing member may be used to support the portion of the continuous length of articles 32 intermediate the heads mainly to keep the portion continuous length of articles 32 from deflecting too much intermediate the heads 40.

In some instances, the laser beam 58 may only score the continuous length of articles 32 and then the discrete article 30 may be fully separated from the continuous length of articles 32 mechanically using the heads 40. In an example, once the scoring occurs, the first head 40 may be driven at a higher angular velocity than the second head for a short time about the orbit about the first rotational axis 38 to separate the discrete article 30. In other instances, once the scoring occurs, the first head 40 may at least partially contract to separate the discrete article 30. In some instances, a second laser system may be provided, with at least a scan head positioned on an opposite side of the continuous length of articles, so that ablating and/or melting or scoring may occur from both sides of the continuous length of articles.

Once the discrete article 30 is separated from the continuous length of articles 32, it may somewhat contract to the configuration illustrated at "A1" in FIG. 2. In some instances, the discrete articles 30 may comprise elastic films or strands, such as belts in pants. Once these elastic films or strands are severed by the anvil-less separation methods, they may help separate other portions (e.g., nonwoven materials) of the discrete articles from the continuous length of the articles owing the elastic contraction of the elastic strands or films upon separation. The contraction of the discrete articles may occur before or after the first head 40 is rotated (if the first head is to be rotated during a particular process). The discrete articles 30 may then be placed on a moving carrier member 60 in the depositing position 48 of the orbit about the first rotational axis 38. The moving carrier member 60 may comprise a moving conveyor, a rotating roll, or a rotating head, for example. In an instance of a rotating head, the rotating head may orbit about a frame of a transfer device at a constant angular velocity or a variable angular velocity. A variable angular velocity may be used to accommodate multiple pitch outputs from the transfer device. An example transfer device is further described in U.S. Pat. No. 6,450,321 to Blumenthal et al., issued on Sep. 17, 2002. Once transferred off the transfer assembly 34, the discrete article 12 may then be moved downstream of the transfer assembly 34 for additional processing or for packaging, for example.

In some instances, it may be desirable to provide a head moveable between an expanded configuration and a contracted configuration. The expanded configuration may be a normal configuration in some cases, without any expansion of the head. The head may then contract into the contracted configuration. In other instances, the contracted configuration may be the normal configuration and the head may expand into the expanded configuration. Those of skill in the art will recognize that there are many ways to expand and/or contract a head, such as by using pneumatics, or hydraulics, for example, and those mechanisms are within the scope of the present disclosure. Some non-limiting examples of adjustable heads are provided herein.

Referring to FIG. 4, example adjustable heads 40 that are configured to move between a first configuration and a second configuration are provided. The first configuration may be the expanded configuration as illustrated in FIG. 4. The heads 40 may comprise a first portion 62, a second portion 64, and an optional third portion 66. The second portion 64 may be moveable relative to the first portion 62, such that the head 40 may expand and contract about the MD or the cross machine direction (CD). The optional third portion 66 may also be moveable relative to the first portion 62, such that the head 40 may expand and contract about the MD or the CD. In an instance, a first end 68 of a first linkage 70 may be rotatably engaged with the first portion 62 and a second end 72 of the first linkage 70 may be rotatable engaged with the second portion 64. If the third portion 66 is provided, a first end 74 of a second linkage 76 may be rotatably engaged with the first portion 62 and a second end 78 of the second linkage 76 may be rotatable engaged with the third portion 66. The first and second linkages 70 and 76 may maintain the first and second heads 40 in the first or expanded configuration, when desired. When the first and second heads 40 are in the first configuration, referring to FIG. 5, the first and second portions 52, 54 of the continuous length of articles 32 on the first and second heads 40, respectively, are stretched into an expanded configuration. A portion of the continuous length of articles 32 between the first and second heads 40 may be ablated and/or melted by the laser beam 58 when the first and second portions 52, 54 of continuous length of articles 32 are in the first or expanded configuration so as to eliminate, or at least reduce, folds, pleats, and/or ridges in the continuous length of articles 32 and provide a higher quality separation owing to the stretching of the continuous length of articles 32. A discrete article 30 may be separated from the continuous length of articles 32 may be separated along a line of separation 31.

Referring to FIG. 6, as the first head 40 (the head on the right in FIG. 4) begins to rotate about the second rotational axis 50, the first and second linkages 70 and 76 may begin to contract the first head. In other instances, the first and second linkages 70 and 76 may maintain the first head 40 in the fully expanded position until rotation about the second rotational axis 50 is complete. A discrete article 30 in the partially rotated position is illustrated in a partially expanded configuration in FIG. 7. By maintaining the first head 40 in the expanded or first configuration, or a partially expanded configuration, during rotation about the second rotational axis 50, better control can be maintained on the discrete article 30 because of the reduced instances of folds, creases, or pleats in the discrete article 30 when stretched or expanded by the head 40. The second ends 72 and 78 of the first and second linkages 70 and 76, respectively, may be rotatably engaged with a wheel 80. The wheel 80 may be configured to rotate in the direction shown by arrow "R" (or the opposite direction as arrow R) in FIGS. 4 and 5 and then in the opposite direction once the head 40 has moved past the depositing position 48. Rotation in the opposite direction will again move the second and third portions 64 and 66 away from the first portion 64. The wheel 80 may have pins or other structures extending therefrom and configured to be joined to the first ends 68 and 74. The pins may be indicated by "A" and "B" in FIGS. 4, 6, and 8. The heads 40 may have a track 83 defined therein. The pins may move about the track 83 when moved by the wheel 80 to cause the first ends 68 and 74 to move relative to the head 40. As the wheel 80 rotates in the direction of arrow R, the second and third portions 64 and 66 are drawn toward the first portion 62 owing to the linkages 70 and 76. The position illustrated in FIG. 8 is the second or contracted configuration of the first head 40. The amount of rotation of the wheel 80 and the length of the linkages 70 and 76 may dictate the distance the second and third portions 64 and 66 are drawn towards or expanded away from the first portion 62. This adjustability of the heads 40 allows the heads 40 to accommodate discrete articles 30 with different pitch lengths. Likewise, in the first configuration or expanded configuration of FIG. 4, the second and third portions 64 and 66 may be extended away from the first portion 62 any suitable distance depending on the desired tensile force to be placed on the continuous length of articles 32 or discrete articles 30 positioned on the head 40. The discrete article 30 in the second configuration or contracted configuration of the head 40 is illustrated in FIG. 9. Fluid ports may be present in the second portion 64 and third portion 66 of the head 40 to maintain control of ends or sides of the discrete articles or portions of the continuous length of discrete articles 32. The second head 40 of FIG. 4 and other heads may operate in a like manner.

In the first configuration of FIG. 4, the first head 40 may have a first length 82 (MD) and in the second configuration of FIG. 8, the first head 40 may have a second, smaller length 84 (CD). In an intermediate configuration of FIG. 7, the first head may have a third length 86 that is the same as the first length 82, less than the first length 82, or greater than or the same as the second length 84. Likewise, in a first configuration, refereeing to FIG. 5, the first portion 52 of the continuous length 32 may have a first pitch length 82' (MD) and, in the second configuration, referring to FIG. 9, the discrete article 30 may have a second, smaller pitch length 84'. In an intermediate configuration, referring to FIG. 7, the discrete article 30 may have a third length 86' that is the same as the first pitch length 82', less than the first pitch length 82', or greater than or the same as the second pitch length 84'.

As an alternative to the heads 40 of FIGS. 4, 6, and 8, referring to FIGS. 10-12, heads 140 may be used. All of the components of the heads 140 and the heads 40 may be the same except for the way in which the heads 140 move between the first configuration (FIG. 10) and the second configuration (FIG. 12). FIG. 11 illustrates the head 140

(head 140 on right of FIG. 10) in a partially contracted configuration. In some instances, the heads 140 may begin to contract prior to the rotation about the second rotational axis 50, during rotation about the second rotational axis 50, or after rotation about the second rotational axis 50. This concept applies to any of the heads of the present disclosure. For the heads 140, the first ends 68 and 74 of the first and second linkages 70, 76, respectively, may be fixed in position regardless of the rotational position of the heads 140 about the second rotational axis 50. As the head 140 rotates about the second rotational axis 50, in the direction indicated by arrow R, or in the opposite direction to arrow R, the first ends 68 and 74 may be fixed in position and may not move. The first ends 68 and 74 may be fixed to a rigid member 180 positioned below the heads 140 so as not to rotate with the heads 140. As an example, the rigid member 180 may have two pins (indicated as "A" and B") extending outwardly therefrom and configured to be engaged with the first ends 68 and 74. The heads 140 may rotate relative to the rigid member 180 and pins about the second rotational axis 50. The pins may be positioned within the track 83 to allow the heads 140 to rotate while the pins, and thereby the first ends 68, 74, remain fixed in position. A discrete article 30 may be separated from the continuous length of articles 32 may be separated along a line of separation 31.

In still other instances, the heads may move between the first configuration and the second figuration using yet another mechanism. Referring to FIGS. 13 and 14, heads 240 may be moved between the first configuration (FIG. 13) and a second configuration (FIG. 14) using a rack and pinion system. In some instances, the first configuration may be an expanded configuration, while the second configuration may be a normal configuration. In other instances, the first configuration may be the normal configuration of the heads 240 and the second configuration may be a contracted configuration. The heads 240 may be rotated about the second rotational axis 50, as explained above, in the direction of arrow R, or in the opposite direction as arrow R. The heads 240 may still comprise the first portion 62, the second portion 64, and an optional third portion 66. The rack and pinion system may comprise a first rack 170 operable engaged with a pinion 172. The first rack 170 may also be engaged with the second portion 64. The rack and pinion system may comprise a second rack 176 operably engaged with the pinion 172. The second rack 176 may also be engaged with the third portion 66. As the pinion 172 is rotated by any suitable drive mechanism, the first and second racks 170 and 176 move linearly, in opposite directions. This causes the second portion 64 and the third portion 66 to move either toward or away from the first portion 62. The second and third portions 64, 66 may be moved any suitable distance from the first portion 62 by the rack and pinion system to accommodate variation levels of tension in discrete articles positioned thereon and/or discrete articles having different pitches. The pinion 172 may comprise teeth that meshingly engage teeth on the racks 170 and 176. The rack and pinion system essentially turns rotational movement of the pinion 172 into linear motion of the racks 170 and 176.

When moving from manufacturing a first discrete article having a first pitch to a second discrete article having a second, different pitch, the racks 170 and 176 may be adjusted by unlocking them and moving them relative to the pinion (inwardly or outwardly) and then relocking them in place. This allows the second and third portions 64, 66 to be moved inwardly (closer to the first portion 62) or outwardly (further away from the first portion 62), before a differently pitched discrete article is transferred.

The pinion 172 may be rotated independently of the first portion 62. In some instances, the pinion 172 may be independent controlled by, for example, a servo motor 67. In such an instance, teeth on a gear 65 driven by the servo motor 67 may be meshingly engaged with teeth on the pinion 172. This allows for adjustment of the racks 170 and 176 relative to the pinion 172 without the need to unlock and relock the racks 170 and 176. This also allows for adjustment when switching between a first discrete article having a first pitch and a second discrete article having a second, different pitch to adjust the travel (e.g., movement of the second and third portions 64, 66 between the first configuration (FIG. 13) and the second configuration (FIG. 14)) of the second and third portions 64, 66, relative to the first portion 62.

Figure 15:
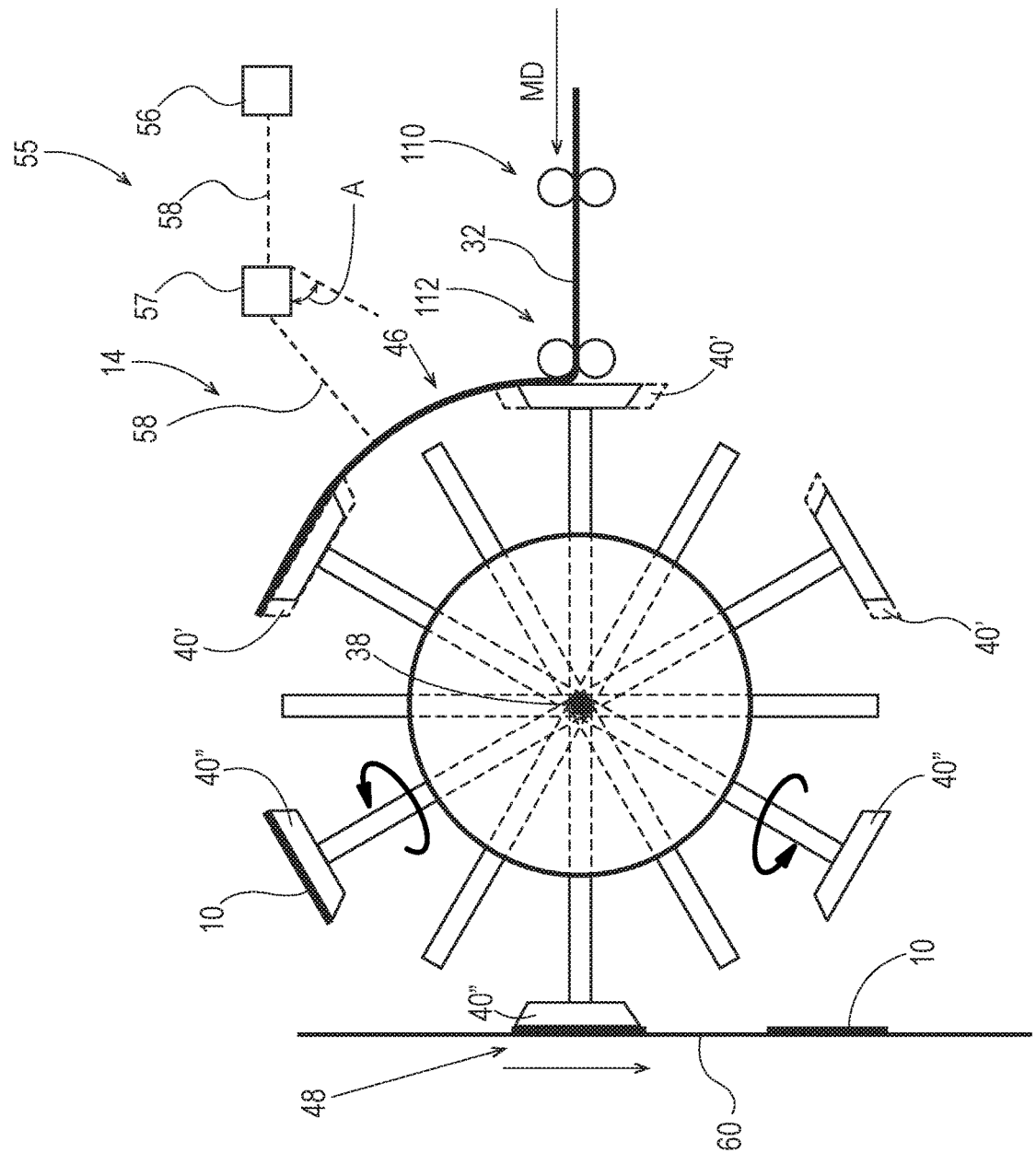
FIG. 15 is a front view schematic illustration of another transfer assembly having a plurality of heads and a laser system that are together configured to separate and position discrete articles formed from a continuous length of articles in accordance with the present disclosure.

Referring to FIG. 15, the heads are illustrated in the first configuration or the second confirmation while orbiting about the first rotational axis 38. The heads of FIGS. 4, 6, and 8 will be used in this example, but it will be understood that the heads 140, 240, or other heads that can move between a first configuration and a second configuration may also be used. In FIG. 15, the heads 40' have the configuration shown in FIG. 4 and the heads 40" have the configuration shown in FIG. 8. The heads 40' may be maintained in, or moved into, the first configuration (e.g., FIG. 4) or the expanded configuration prior to engaging the continuous length of articles 32. The heads 40' may be maintained in the first configuration through the laser beam 58 ablating and/or melting step, potentially through the rotation about the second rotational axis 50, and then the heads 40' may move into the second configuration (e.g., heads 40") after the laser beam ablating or separating step and/or after the rotation about the second rotational axis 50. A method may comprise extending the discrete article 30 more proximate to the receiving position 46 of the orbit about the first rotational axis 38 than the depositing position 48 of the orbit about the first rotational axis 38. The method may comprise at least partially, or fully, relaxing the discrete article 30 during the rotation about the second rotational axis 50 or after or before the rotation about the second rotational axis 50. In other instances, the method may comprise at least partially relaxing the discrete article 30 during or before rotation about the second rotational axis 50 and at least partially, or fully relaxing the discrete article 30 after rotation about the second rotational axis 50.

The transfer assembly 34 may be provided with certain features to make it at least somewhat pitch-less or capable of handling more than one size or pitch (MD length) of discrete articles. Stated another way, the transfer assembly 34 may be fed by the continuous length of articles 32 having different elastic tensions in the machine direction (i.e., degrees of tensioning of the elastics in the continuous length of articles 32) to make the transfer assembly 34 suitable for transferring more than one size or pitch of discrete articles. Referring again to FIG. 15, a first set of nip rolls 110 and a second set of nip rolls 112 may be provided on the infeed side of the transfer assembly 34. The first set of nip rolls 110 may rotate at a first rotational speed and the second set of nip rolls 112 may rotate at a second, different rotational speed or at the same rotational speed in some instances. The continuous length of articles 32 before it arrives at the first set of nip rolls 110 will be under at least some elastic tension in the machine direction. The first and second sets of nip rolls 110, 112 may be used to decrease the elastic tension in the machine direction in the continuous length of articles 32 intermediate the first and second sets of nip rolls 110, 112. For example, if the transfer assembly 34 is running a size three diaper with a first pitch (assume first and second nip rolls have the same rotational speed) and then it is desired to run a size five diaper with a second, larger pitch, the first set of nip rolls 110 may rotate with a faster rotational speed as the rotational speed of the second set of nip rolls 112 to relax or reduce the elastic tension in the machine direction in the continuous length of articles 32 intermediate the first and second nip rolls 110, 112. This allows a commonly pitched portion of the continuous length of articles 32 (i.e., same pitch as the size three diaper) to be provided to the first head 40. Instead of using nip rolls to accomplish the common pitch, other driven web transport surfaces having a high enough coefficient of friction to reduce the elastic tension in the machine direction in the continuous length of articles 32 may be used, as will be recognized by those of skill in the art.

Methods may comprise providing a first portion of the continuous length of articles 32 to the first head 40 while producing a first article having a first final pitch and providing a first portion of the continuous length of articles 32 to the first head 40 while producing a second article having a second final pitch. The second final pitch may be larger or smaller than the first final pitch. The first portion provided to the first head 40 for the first article has a first pitch. The first portion provided to the first head 40 for the second articles has the first pitch. The methods may comprise machine directional relaxing or tensioning the first portion of the first continuous length of articles before providing the same to the first head 40. In essence, the methods enable providing commonly pitched first portions to the first head, while producing articles having different final pitches. This enables a single transfer assembly to be configured to for use with multiple sizes or final pitches of articles and significantly reduced change over times.

Figure 16:
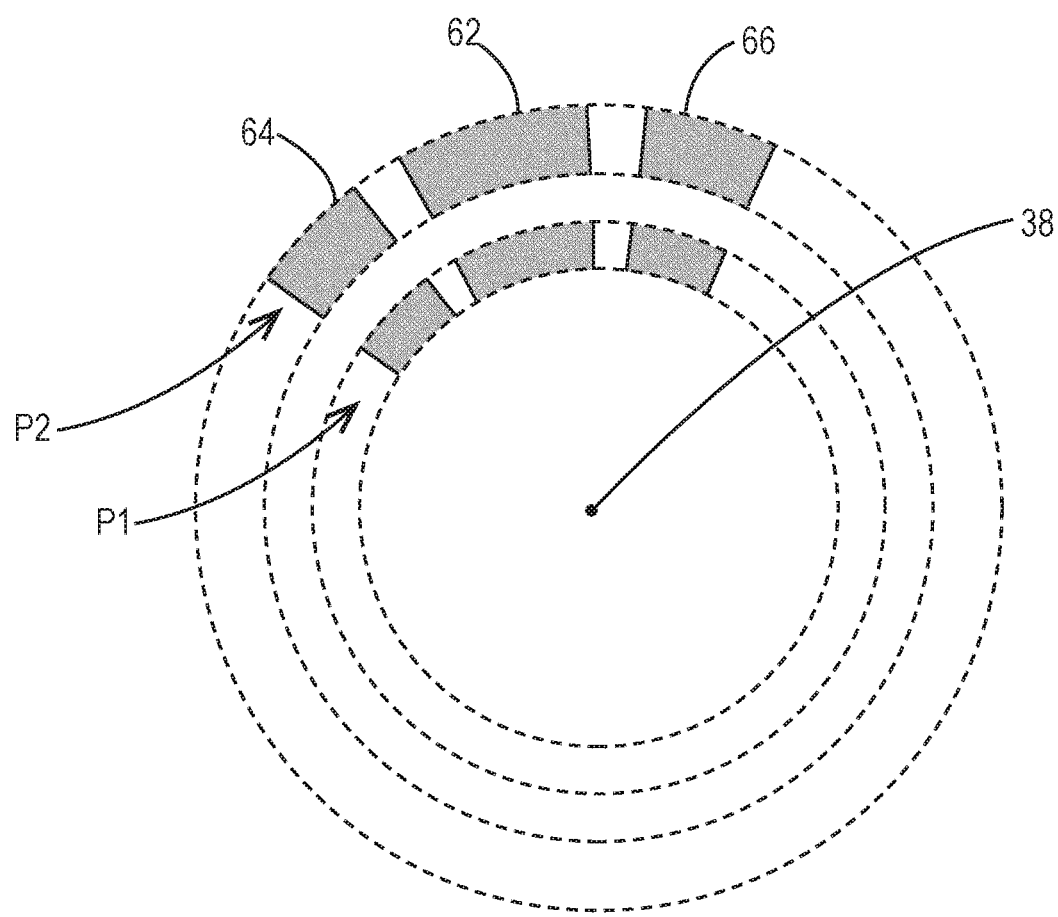
FIG. 16 is a schematic illustration of heads moving radially relative to a rotation axis to accommodate a large number of pitches of discrete articles in accordance with the present disclosure.

Referring to FIG. 16, the heads 40 may be moved radially inwardly and/or radially outwardly relative to the rotational axis 38 to accommodate different pitch lengths of discrete articles. The first portion 62, the second portion 64, and the third portion 64 may be moved radially from position 1 ("P1") to position 2 ("P2") to accommodate discrete articles having larger pitch lengths. Alternatively, the first portion 62, the second portion 64, and the third portion 64 may be moved radially from position 2, P2, to position 1, P1, to accommodate discrete articles having smaller pitch lengths.

Figure 17:
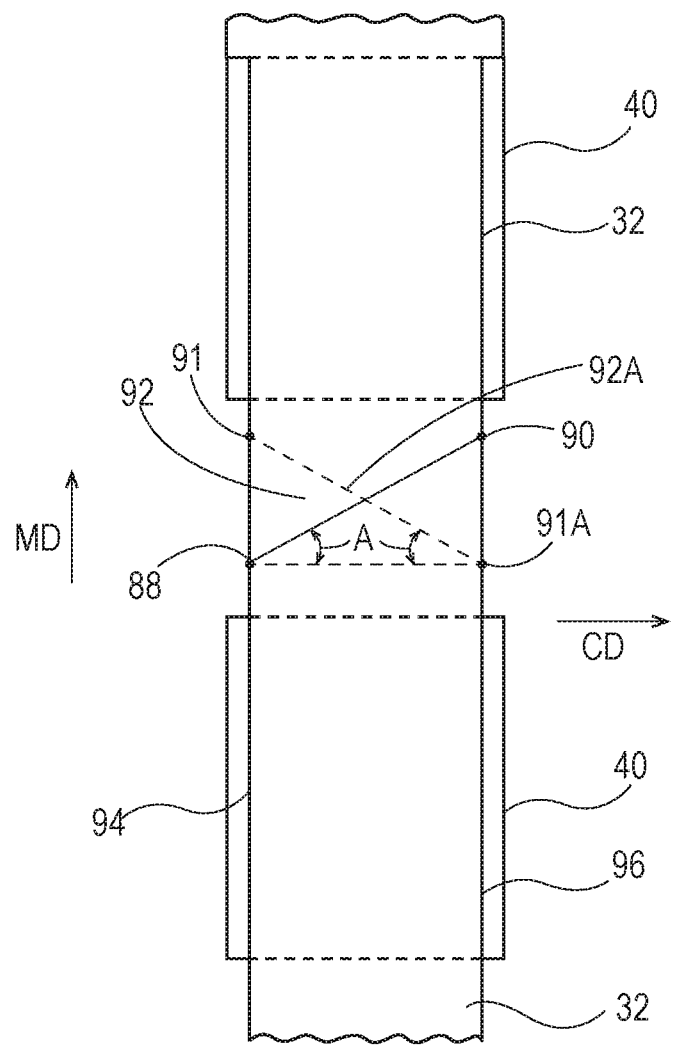
FIG. 17 is a top view schematic illustration of a first portion of the continuous length of articles being separated from a second portion of the continuous length of articles while the first portion and the second portion are positioned at least partially on the first and second heads in accordance with the present disclosure.

Referring to FIG. 17, the scan head 57 may direct the laser beam 58 such that the laser beam 58 traverses the continuous length of articles 32 during the ablating or melting step. Stated another way, the laser beam 58 may be directed by the scan head 57 from a first side 94 of the continuous length of articles 32 to a second, opposite side 96 of the continuous length of articles 32 during the ablating step. The laser beam 58 may be directed by the scan head 57 from point 88 to point 90 at an angle, A, relative to the CD to ablate or melt the continuous length of articles 32 along an ablation line 92. The laser beam 58 may be directed at an angle, A, by the scan head 57 to accommodate for the MD speed of the continuous length of articles 32. The laser beam 58 may be directed at an angle, relative to the CD and the MD, by the scan head 57 for the same purpose. Although an angled ablation (relative to the CD) is shown between points 88 and 90 in FIG. 11, in reality, this will produce a straight ablation owing to the MD speed of the continuous length of articles 32. If the continuous length of articles 32 is moving at the same linear speed as the laser beam 58, the angle may be 45 degrees, or about 45 degrees. If the continuous length of articles 32 has a slower linear speed than the laser beam 58, the angle, A, may be less than 45 degrees to achieve a straight ablation. If the continuous length of articles 32 has a higher linear speed than the laser beam 58, the angle, A, may be greater than 45 degrees to achieve a straight ablation. The laser beam 58 may also be directed in other paths, such as a sinusoidal path, by the scan head 57 while traversing the continuous length of articles 32 during the ablation or melting step as will be understood to those of skill in the art.

Once the ablation is made, the laser beam's focal point may be directed back to point 88 for the next ablation by the scan head 57. The laser beam 58 may be cycled off until it is returned to point 88 so as to not ablate an undesired portion of the continuous length of articles 32. In other instances, the laser beam's focal point may by directed by the scan head 57 to point 90A and then ablate from the second side 96 back towards the first side 94 along ablation line 92A, at the same angle, A, when another ablation is desired. In such an instance, the laser beam 58 may not need to be cycled off, but still could be on between ablations. Once the laser beam 58 is directed by the scan head 57 to at point 91, it may then be directed by the scan head 57 to point 88 for the process to repeat. The laser beam 58 may also be directed along other paths by the scan head 57 while traversing the continuous length of articles 32 during the ablation or melting step as will be understood to those of skill in the art.

By providing the transfer assembly 34 with heads 40 that may move from a first configured to a second configuration, the transfer assembly 34 may accommodate a large range of pitch lengths. This feature is provided by the heads 40 that may expand and/or contract to accommodate different lengths of material or discrete articles. As such, in a first arrangement of the transfer assembly 34, or first arrangement (first expanded/contracted state) of the heads 40, the discrete articles being formed thereon may have a first pitch length requirement. In a second arrangement of the transfer assembly 34, or second arrangement (second, different expanded/contracted state) of the heads 40, the discrete articles being formed thereon may have a second, different pitch length requirement. The second, different pitch length requirement may be larger or smaller than the first pitch length requirement. A pitch length requirement may be equated, in some instances, to diaper sizes, for example.

To accommodate a larger pitch length, the heads 40 may be moved radially outwardly relative to the first rotational axis 38 and to accommodate a smaller pitch length, the heads 40 may be moved radially inwardly relative to the first rotational axis 38. As the heads are moved radially inwardly or outwardly relative to the first rotational axis 38, the point at which the laser beam 58 contacts the continuous length of articles 32 may also need to be moved radially inwardly or outwardly. The point or line at which the laser beam 58 contacts the continuous length of articles 32 may be referred to as the laser beam/continuous length of articles interface. The laser beam/continuous length of articles interface may be a first radial distance from the first rotational axis 38 in a first arrangement of the transfer assembly 34 to produce a first pitch of the discrete articles 30. The laser beam/continuous length of articles interface may be a second, different radial distance from the first rotational axis 38 in a second arrangement of the transfer assembly 34 to produce a second, different pitch of the discrete articles 30. In essence, the laser beam/continuous length of articles interface may be moved radially outwardly and radially inwardly depending on what pitch length is desired or required in the discrete articles 30.

Figure 18:
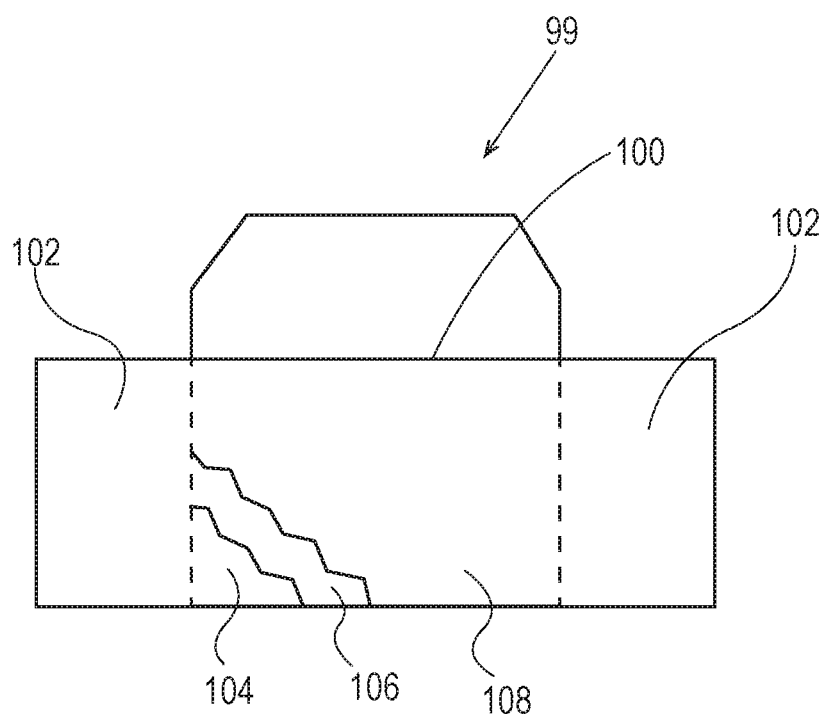
FIG. 18 is a top view schematic illustration of an example discrete article capable of being separated from a continuous length of articles by the transfer assemblies in accordance with the present disclosure.

The heads 40 may have any suitable configuration, size, and/or shape depending on what discrete articles is being transferred. Referring to FIG. 18, for example, an absorbent article 99 may have a chassis region 100 comprising a topsheet 104, a backsheet 108, and an absorbent core 106. The backsheet 108 may also comprise an outer cover nonwoven material. Side panels 102 that may comprise elastic stands or films may be positioned outboard of the chassis 100. Instead of the side panels, belts may be provided on absorbent articles. The belts may have one or more elastic strands or films. The elastic stands or elastic films in the side panels or belts may be helpful in fully separating an absorbent article from a continuous length of absorbent articles once at least partially separated by the anvil-less methods of separation described herein. The elastic strands or films, once cut, may help separate portions of other materials in the absorbent articles, such as nonwoven materials, for example. Heads, like the example heads illustrated herein, may be made to accommodate and fit such discrete absorbent articles.

The laser systems used herein may be any suitable type of laser systems for separating discrete articles from a continuous web of the articles. Certain laser systems may be more suitable for ablating certain types of materials. For example, discrete articles that comprise films may be more easily separated by a certain type of laser than nonwoven materials, for example. Examples lasers that may be used to separate discrete articles may be CO2 laser systems, ultra-short pulse laser systems, and long pulse laser systems.

Figure 19:
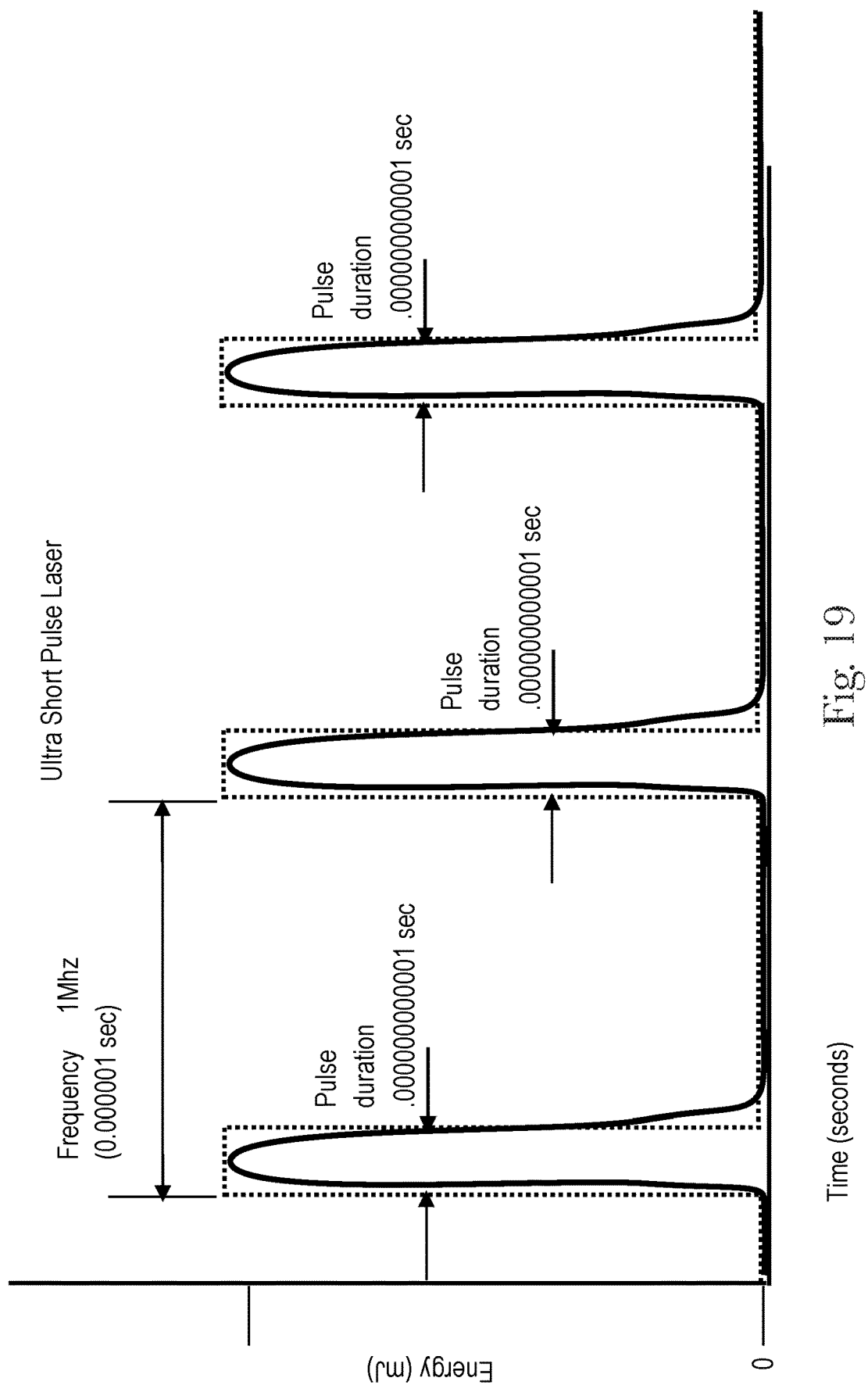
FIG. 19 graphically illustrates the pulse duration and frequency of an ultra-short pulse laser in accordance with the present disclosure.

As some background on laser systems, each laser source operates at a certain pulse duration and frequency. The pulse duration, also referred to herein as pulse, is the period of time over which the laser beam imparts energy to the material. The frequency is the time period starting from the beginning of a first pulse and ending at the beginning of the next, subsequent pulse, as illustrated, for example in FIGS. 19 and 20. Different types of lasers have different pulse durations. Lasers that have a relatively longer pulse duration, referred to herein as longer-pulse lasers, generally remove material or cut material thermally. By contrast, ultra-short pulse lasers have a relatively short pulse duration, as illustrated in FIG. 19. The pulse duration and frequency change how the laser beam interacts with the substrate (e.g., nonwoven, film, nonwoven/film laminate). Generally, the laser energy is absorbed by the material, which may be a substrate, resulting in an increase in temperature at and/or near the area of absorption. As the temperature of that material increases to the melting point, material is removed by conventional melting and vaporization. However, because the longer pulse lasers have a longer pulse duration and longer frequency, longer pulse lasers cause the temperature of the material to increase, resulting in melting of the substrate and sometimes an undesirable heat modified zone. By contrast, for ultra-short pulse lasers, which have short pulse durations and short frequency, the temperature rise in the area to be cut may be fast and short, resulting in thermal ablation. One advantage of ultra-short pulse lasers over longer-pulse lasers is that the ultra-short pulse lasers deposit energy so quickly that the material ablates before having the time to melt the adjacent areas of the material. An ultra-short pulse laser converts portions of the material from a solid state to a gaseous state with minimal effect on the area adjacent the cut edge. Thus, using a longer-pulse laser results in a greater heat modified zone than using an ultra-short pulse laser.

Figure 20:
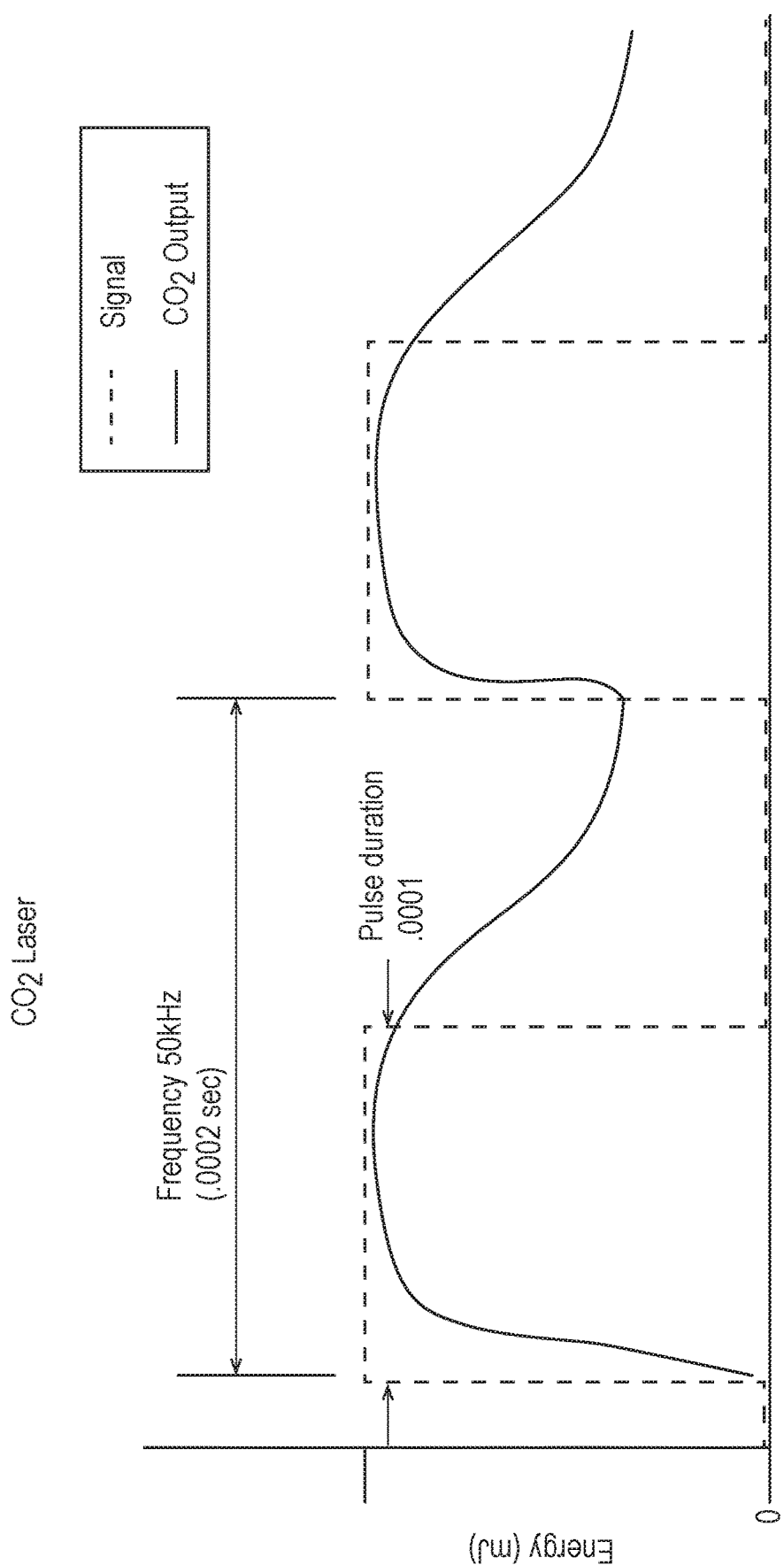
FIG. 20 graphically illustrates the pulse duration and frequency of a CO2 laser in accordance with the present disclosure.

Ultra-short pulse lasers refer to lasers having pulse durations less than about 100 picoseconds ($10^{-12}$). Ultra-short pulse lasers may have pulse durations on the order of femtoseconds ($10^{-15}$). Ultra-short pulse lasers are distinguishable from continuous wave lasers and longer-pulse lasers, which may have a pulse duration of nanoseconds ($10^{-9}$). Examples of ultra-short pulse lasers include Ti-Sapphire and Dye lasers. Ultra-short pulse lasers are available to be supplied, for example, by Amphos Inc. of West Springfield, Mass.; TRUMPF Inc. of Farmington, Conn.; and ROFIN-SINAR Laser GmbH of Hamburg, Germany. Similarly, examples of continuous wave lasers and longer-pulse lasers include $CO_2$ and Nd:Yag. FIGS. 19 and 20 graphically depict the difference in the pulse duration and frequency of an ultra-short pulse laser, FIG. 19, and a $CO_2$ laser, FIG. 20.

Referring to FIG. 19, the ultra-short pulse laser is able to operate at relatively high frequencies and relatively short pulse durations. For example, the frequency of the ultra-short pulse laser may be 1 MHz (0.000001 seconds) and the pulse duration may be 1 picosecond (0.000000000001 seconds). It is to be appreciated that the pulse duration is one million times shorter than the period, which is the inverse of the frequency. The ultra-short pulse laser is configured to output energy during the pulse duration. Because the energy is output at such a short interval of time, the thermal effects due to the energy imparted to the substrate are minimized. Stated another way, the pulse duration, the time that energy is imparted to the substrate, is short compared to the thermal diffusion time of the material of the substrate. Thus, there is no or very limited time for the heat to diffuse and the material adjacent the laser beam to melt, forming accumulation bulbs and/or clusters and/or altering the properties of the material. Further, the frequency of the ultra-short pulse laser is relatively high. The frequency is the time from the start of a first pulse duration to the start of the next, subsequent pulse duration. Frequency is measured as a cycle/second. Thus, during a single cycle, energy is imparted to the substrate during the pulse duration and the remainder of the time, no or minimal energy is imparted to the substrate because the decay time for the ultra-short pulse laser is almost instantaneous. This allows for relatively high energy to be imparted to web over repeated, short periods of time. Due to relatively short frequency, short pulse duration, and precision of the ultra-short pulse lasers, there is a lower dependence on wavelength and an ability to machine materials that have a greater heat sensitivity.

By contrast, FIG. 20 graphically illustrates the frequency and pulse duration of a $CO_2$ laser, which is considered to be a longer pulse laser. As illustrated, the pulse duration is much longer than that of the ultra-short pulse laser. In application, when this laser is used quickly, the laser is unable to recover such that there are clear, defined pulse durations. As illustrated in FIG. 20, after the laser imparts energy to the substrate during the pulse duration, the laser imparts no energy to the substrate during the remainder of the cycle. During the time that the signal passed to the laser source instructs the laser source not to impart energy to the substrate, the laser source tapers off over a period of time, referred to as the decay time, as shown by the output. Generally, the tapering off is longer than the pulse duration. As illustrated by the graphs, the decay time is much faster for the ultra-short pulse laser. Further, the $CO_2$ laser is unable to output energy over as short a period of time as compared to the ultra-short pulse laser. Rather, the $CO_2$ laser imparts energy over a longer pulse duration which allows the material to heat up during cutting and may result in a more undesirable cut edge as compared with the cut edge formed by the ultra-short pulse laser.

It is also to be appreciated that the wavelength of ultra-short pulse lasers and longer pulse lasers are different. The wavelength of the ultra-short pulse laser is less than about 1 micron. For example, the wavelength of the ultra-short pulse laser may be from about 300 nanometers to about 1080 nanometers, specifically reciting all 0.1 nanometer increments within the specified range. In some forms, the wavelength of the ultra-short pulse laser may be from about 1000 nm to about 1080 nm, from about 1020 nm to about 1070 nm, or from about 1030 nm to about 1050 nm, specifically reciting all 0.1 nm increments within the specified ranges and all ranges formed therein or thereby. Generally, each different material has a wavelength or range of wavelengths at which its absorptivity is greatest or optimal. Thus, a laser source may be chosen such that the wavelength emitted by the laser is more readily absorbed by the substrate. It is to be appreciated that materials may be altered to increase their absorptivity even if the laser source is operating outside their optimal range of wavelengths. In some instances, the substrate may be chemically altered such that the substrate has an increased rate of energy absorption or absorptivity. It is believed that due to the pulse duration at which the ultra-short pulse laser operates and the great amount of energy imparted to the substrate over such a short period of time, the ultra-short pulse laser is able to modify materials that have a greater heat sensitivity, and, thus, are less dependent on the wavelength at which the absorptivity is greatest or optimal.

EXAMPLES/COMBINATIONS

A. A method of separating and positioning discrete articles formed from a continuous length of articles, the method comprising the steps of:
 advancing the continuous length of articles in a machine direction;
 providing a transfer assembly comprising:
  a frame defining a first rotational axis;
  a first head comprising a first transfer surface;
  a second head comprising a second transfer surface;
 orbiting the first head about the first rotational axis;
 orbiting the second head about the first rotational axis;
 receiving a first portion of the continuous length of articles on the first transfer surface of the first head in a receiving position of the orbit about the first rotational axis;
 subsequently, receiving a second portion of the continuous length of articles on the second transfer surface of the second head in the receiving position of the orbit about the first rotational axis;
 providing a laser system configured to produce and direct a laser beam;
 ablating a portion of the continuous length of articles intermediate the first head and the second head with the laser beam to separate the first portion of the continuous length of articles from the second portion of the continuous length of articles, forming a discrete article on the first head;
 wherein the ablating step comprises traversing the portion of the continuous length of articles with the laser beam at an angle relative to a cross-machine direction and the machine direction from a first side of the continuous length of articles to a second, opposite side of the continuous length of articles; and
 placing the discrete article on a moving carrier member in a depositing position of the orbit about the first rotational axis.

B. The method of Paragraph A, comprising:
 rotating the first head through the receiving position of the orbit about the first rotational axis in a first configuration; and
 rotating the first head through the depositing position of the orbit about the first rotational axis in a second, different configuration.

C. The method of Paragraph A, wherein the first head comprises a first portion and a second portion, wherein the second portion is moveable relative to the first portion, comprising moving the first head between a first configuration and a second configuration, wherein, in the first configuration, the first head has a first length, wherein, in the second configuration, the first head has a second length, and wherein the second length is smaller than the first length, comprising:
 maintaining the first head in the first configuration prior to the ablating step; and
 moving the first head into the second configuration subsequent to the ablating step.

D. The method of Paragraph A, comprising:
 rotating the first head and the discrete article about a second rotational axis during the orbiting about the first rotational axis;
 wherein the first rotational axis extends in a first direction, wherein the second rotational axis extends in a second, direction, and wherein the second direction is generally perpendicular to the first direction.

E. A method of separating and positioning discrete articles formed from a continuous length of articles, the method comprising the steps of:
 advancing the continuous length of articles in a machine direction;
 providing a transfer assembly comprising:
  a frame defining a first rotational axis;
  a first head comprising a first transfer surface, wherein the first transfer surface defines a first plurality of fluid ports;
  a second head comprising a second transfer surface, wherein the second transfer surface defines a second plurality of fluid ports;
 orbiting the first head about the first rotational axis;
 orbiting the second head about the first rotational axis;
 applying a fluid pressure to the first plurality of fluid ports;
 applying a fluid pressure to the second plurality of fluid ports;
 receiving a first portion of the continuous length of articles on the first transfer surface of the first head in a receiving position of the orbit about the first rotational axis;
 subsequently, receiving a second portion of the continuous length of articles on the second transfer surface of the second head in the receiving position of the orbit about the first rotational axis;
 using a means for separating a portion of the continuous length of articles intermediate the first head and the second head to separate the first portion of the continuous length of articles from the second portion of the continuous length of articles, forming a discrete article on the first head;
 wherein the means for separating traverses the portion of the continuous length of articles from a first side of the continuous length of articles to a second, opposite side of the continuous length of articles;
 rotating the first head and the discrete article about a second rotational axis during the orbiting about the first rotational axis;

wherein the first rotational axis extends in a first direction, and wherein the second rotational axis extends in a second, different direction; and placing the discrete article on a moving carrier member in a depositing position of the orbit about the first rotational axis.

F. A method of separating and positioning discrete articles formed from a continuous length of articles, the method comprising the steps of:

advancing the continuous length of articles in a machine direction;

providing a transfer assembly comprising:
- a frame defining a first rotational axis;
- a first head comprising a first transfer surface, wherein the first transfer surface defines a first plurality of fluid ports;
- a second head comprising a second transfer surface, wherein the second transfer surface defines a second plurality of fluid ports;

orbiting the first head about the first rotational axis;
orbiting the second head about the first rotational axis;
applying a fluid pressure to the first plurality of fluid ports;
applying a fluid pressure to the second plurality of fluid ports;
receiving a first portion of the continuous length of articles on the first transfer surface of the first head in a receiving position of the orbit about the first rotational axis;
subsequently, receiving a second portion of the continuous length of articles on the second transfer surface of the second head in the receiving position of the orbit about the first rotational axis;
providing an anvil-less separation means;
separating a portion of the continuous length of articles intermediate the first head and the second head with the anvil-less separation means to separate the first portion of the continuous length of articles from the second portion of the continuous length of articles, forming a discrete article on the first head;
rotating the first head and the discrete article about a second rotational axis during the orbiting about the first rotational axis;
wherein the first rotational axis extends in a first direction, and wherein the second rotational axis extends in a second, different direction; and
placing the discrete article on a moving carrier member in a depositing position of the orbit about the first rotational axis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of separating and positioning discrete articles formed from a continuous length of articles, the method comprising the steps of:

advancing the continuous length of articles in a machine direction;

providing a transfer assembly comprising:
- a frame defining a first rotational axis;
- a first head comprising a first transfer surface, wherein the first transfer surface defines a first plurality of fluid ports; and
- a second head comprising a second transfer surface, wherein the second transfer surface defines a second plurality of fluid ports;

wherein the first head comprises a first portion and a second portion, wherein the second portion is moveable relative to the first portion, comprising moving the first head between a first configuration and a second configuration, wherein, in the first configuration, the first head has a first length in a first direction, wherein, in the second configuration, the first head has a second length in the first direction, and wherein the second length is smaller than the first length;

orbiting the first head about the first rotational axis;
orbiting the second head about the first rotational axis;
applying a fluid pressure to the first plurality of fluid ports;
applying a fluid pressure to the second plurality of fluid ports;
receiving a first portion of the continuous length of articles on the first transfer surface of the first head in a receiving position of the orbit about the first rotational axis;
subsequently, receiving a second portion of the continuous length of articles on the second transfer surface of the second head in the receiving position of the orbit about the first rotational axis;
providing a laser system configured to produce and direct a laser beam;
ablating a portion of the continuous length of articles intermediate the first head and the second head with the laser beam to separate the first portion of the continuous length of articles from the second portion of the continuous length of articles, forming a discrete article on the first head;
wherein the ablating step comprises traversing the portion of the continuous length of articles with the laser beam from a first side of the continuous length of articles to a second, opposite side of the continuous length of articles;
maintaining the first head in the first configuration prior to the ablating step;
moving the first head into the second configuration subsequent to the ablating step;
rotating the first head and the discrete article about a second rotational axis during the orbiting about the first rotational axis;

wherein the first rotational axis extends in a first direction, and wherein the second rotational axis extends in a second, different direction; and placing the discrete article on a moving carrier member in a depositing position of the orbit about the first rotational axis.

2. The method of claim 1, wherein the first head comprises a third portion, wherein the first portion is positioned intermediate the second portion and the third portion, and wherein the third portion is movable relative to the first portion.

3. The method of claim 2, comprising:
maintaining the first head in the first configuration prior to the ablating step; and
moving the first head into the second configuration subsequent to the ablating step.

4. The method of claim 1, wherein the discrete article has a first pitch length in the first configuration of the first head, wherein the discrete article has a second pitch length in the second configuration of the first head, and wherein the first pitch length is greater than the second pitch length.

5. The method of claim 1, comprising orbiting the first head about the first rotational axis at a constant angular velocity between the receiving position and the depositing position.

6. The method of claim 1, comprising orbiting the first head about the first rotational axis at a variable angular velocity at least partially between the receiving position and the depositing position.

7. The method of claim 1, wherein, in a first arrangement of the transfer assembly, the discrete article has a first pitch length requirement, and wherein, in a second arrangement of the transfer assembly, the discrete article has a second, different pitch length requirement.

8. The method of claim 7, comprising providing a laser beam/continuous length of articles interface positioned intermediate the first head and the second head, wherein the laser beam/continuous length of articles interface, in the first arrangement of the transfer assembly, is a first radial distance from the first rotational axis, and wherein the laser beam/continuous length of articles interface, in the second arrangement of the transfer assembly, is a second, different radial distance from the first rotational axis.

9. The method of claim 1, comprising:
rotating the first head through the receiving position of the orbit about the first rotational axis in an expanded configuration; and
rotating the first head through the depositing position of the orbit about the first rotational axis in a contracted configuration.

10. The method of claim 9, comprising extending the discrete article more proximate to the receiving position of the orbit than in the depositing position of the orbit.

11. The method of claim 9, comprising at least partially contracting the first head during the rotating the discrete article about the second rotational axis step to at least partially relax the discrete article.

12. The method of claim 1, wherein the discrete article is a diaper comprising a topsheet, a backsheet, and an absorbent core disposed intermediate the topsheet and the backsheet.

13. The method of claim 1, wherein the ablating step comprises traversing the continuous length of articles with the laser beam at an angle transverse to the cross-machine direction, and wherein the angle is dependent on a machine direction speed of the continuous length of the articles.

14. The method of claim 1, wherein the laser source comprises:
a laser generator configured to emit the laser beam; and
a scan head configured to direct to the laser beam.

15. A method of separating and positioning discrete articles formed from a continuous length of articles, the method comprising the steps of:
advancing the continuous length of articles in a machine direction;
providing a transfer assembly comprising:
a frame defining a first rotational axis;
a first head comprising a first transfer surface;
a second head comprising a second transfer surface;
wherein the first head comprises a first portion and a second portion, wherein the second portion is moveable relative to the first portion, comprising moving the first head between a first configuration and a second configuration, wherein, in the first configuration, the first head has a first length in a first direction, wherein, in the second configuration, the first head has a second length in the first direction, and wherein the second length is smaller than the first length;
orbiting the first head about the first rotational axis;
orbiting the second head about the first rotational axis;
receiving a first portion of the continuous length of articles on the first transfer surface of the first head in a receiving position of the orbit about the first rotational axis;
subsequently, receiving a second portion of the continuous length of articles on the second transfer surface of the second head in the receiving position of the orbit about the first rotational axis;
providing a laser system configured to produce and direct a laser beam;
ablating a portion of the continuous length of articles intermediate the first head and the second head with the laser beam to separate the first portion of the continuous length of articles from the second portion of the continuous length of articles, forming a discrete article on the first head;
wherein the ablating step comprises traversing the portion of the continuous length of articles with the laser beam at an angle transverse to a cross-machine direction and the machine direction from a first side of the continuous length of articles to a second, opposite side of the continuous length of articles; and
placing the discrete article on a moving carrier member in a depositing position of the orbit about the first rotational axis.

16. The method of claim 15, comprising:
rotating the first head through the receiving position of the orbit about the first rotational axis in a first configuration; and
rotating the first head through the depositing position of the orbit about the first rotational axis in a second, different configuration.

17. The method of claim 15, comprising:
maintaining the first head in the first configuration prior to the ablating step; and
moving the first head into the second configuration subsequent to the ablating step.

18. The method of claim 15, comprising:
rotating the first head and the discrete article about a second rotational axis during the orbiting about the first rotational axis;

wherein the first rotational axis extends in a first direction, wherein the second rotational axis extends in a second, direction, and wherein the second direction is generally perpendicular to the first direction.

19. A method of separating and positioning discrete articles formed from a continuous length of articles, the method comprising the steps of advancing the continuous length of articles in a machine direction; providing a transfer assembly comprising: a frame defining a first rotational axis; a first head comprising a first transfer surface, wherein the first transfer surface defines a first plurality of fluid ports; wherein the first head comprises a first portion and a second portion, wherein the second portion is moveable relative to the first portion, comprising moving the first head between a first configuration and a second configuration, wherein, in the first configuration, the first head has a first length in a first direction, wherein, in the second configuration, the first head has a second length in the first direction, and wherein the second length is smaller than the first length; a second head comprising a second transfer surface, wherein the second transfer surface defines a second plurality of fluid ports; orbiting the first head about the first rotational axis; orbiting the second head about the first rotational axis; applying a fluid pressure to the first plurality of fluid ports; applying a fluid pressure to the second plurality of fluid ports; receiving a first portion of the continuous length of articles on the first transfer surface of the first head in a receiving position of the orbit about the first rotational axis; subsequently, receiving a second portion of the continuous length of articles on the second transfer surface of the second head in the receiving position of the orbit about the first rotational axis; using a means for separating a portion of the continuous length of articles intermediate the first head and the second head to separate the first portion of the continuous length of articles from the second portion of the continuous length of articles, forming a discrete article on the first head; wherein the means for separating traverses the portion of the continuous length of articles from a first side of the continuous length of articles to a second, opposite side of the continuous length of articles; maintaining the first head in the first configuration prior to the separating step; moving the first head into the second configuration subsequent to the separating step; rotating the first head and the discrete article about a second rotational axis during the orbiting about the first rotational axis; wherein the first rotational axis extends in a first direction, and wherein the second rotational axis extends in a second, different direction; and placing the discrete article on a moving carrier member in a depositing position of the orbit about the first rotational axis.

* * * * *